(12) United States Patent
Ishihara et al.

(10) Patent No.: US 11,548,857 B2
(45) Date of Patent: Jan. 10, 2023

(54) BIODEGRADABLE COMPOUND, LIPID PARTICLE, COMPOSITION COMPRISING LIPID PARTICLE, AND KIT

(71) Applicant: KABUSHIKI KAISHA TOSHIBA, Minato-ku (JP)

(72) Inventors: Mitsuko Ishihara, Setagaya (JP); Eiichi Akahoshi, Shinagawa (JP); Katsuyuki Naito, Bunkyo (JP); Emi Nozaki, Shinagawa (JP); Saeko Saruwatari, Kawasaki (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 17 days.

(21) Appl. No.: 16/812,625

(22) Filed: Mar. 9, 2020

(65) Prior Publication Data

US 2020/0270217 A1    Aug. 27, 2020

Related U.S. Application Data

(63) Continuation of application No. PCT/JP2019/010681, filed on Mar. 14, 2019.

(30) Foreign Application Priority Data

Aug. 21, 2018   (JP) .............................. JP2018-154955

(51) Int. Cl.
| | | |
|---|---|---|
| *C07D 243/08* | (2006.01) |
| *C07C 229/30* | (2006.01) |
| *C07D 233/02* | (2006.01) |
| *C07D 241/04* | (2006.01) |
| *C07D 211/14* | (2006.01) |
| *A61K 9/127* | (2006.01) |
| *A61K 31/7088* | (2006.01) |

(52) U.S. Cl.
CPC .......... *C07D 243/08* (2013.01); *A61K 9/1271* (2013.01); *C07C 229/30* (2013.01); *C07D 211/14* (2013.01); *C07D 233/02* (2013.01); *C07D 241/04* (2013.01); *A61K 31/7088* (2013.01)

(58) Field of Classification Search
CPC ................ C07D 243/08; C07D 211/14; C07D 233/02; C07D 241/04; A61K 9/1271; A61K 31/7088; C07C 229/30
USPC ........................................................ 514/218
See application file for complete search history.

(56) References Cited

U.S. PATENT DOCUMENTS

| | | | |
|---|---|---|---|
| 8,173,170 B2 | 5/2012 | Niitsu et al. |
| 9,012,498 B2 | 4/2015 | Manoharan et al. |
| 9,061,063 B2 | 6/2015 | Maier et al. |
| 9,463,247 B2 | 10/2016 | Ansell et al. |
| 9,708,628 B2 | 7/2017 | Tange et al. |
| 10,167,253 B2 | 1/2019 | Adami et al. |
| 10,182,987 B2 | 1/2019 | Harashima et al. |
| 2010/0055168 A1* | 3/2010 | Dande .................. A61K 9/1271 424/450 |
| 2011/0200527 A1 | 8/2011 | Xu et al. |
| 2013/0243689 A1 | 9/2013 | Amiji et al. |
| 2016/0376229 A1 | 12/2016 | Adami et al. |
| 2018/0065920 A1 | 3/2018 | Manoharan et al. |
| 2019/0076358 A1 | 3/2019 | Ishihara et al. |
| 2019/0218180 A1 | 7/2019 | Suzuki et al. |
| 2020/0000723 A1 | 1/2020 | Ishihara et al. |

FOREIGN PATENT DOCUMENTS

| | | |
|---|---|---|
| EP | 3860561 A1 | 8/2021 |
| JP | 2013-523651 A | 6/2013 |
| JP | 2015-500835 A | 1/2015 |
| JP | 2015-505838 A | 2/2015 |
| JP | 5808064 B2 | 11/2015 |
| JP | 5817053 B2 | 11/2015 |
| JP | 5893611 B2 | 3/2016 |
| JP | 2016-121174 A | 7/2016 |
| JP | 6044920 B2 | 12/2016 |
| JP | 6093710 B2 | 3/2017 |
| JP | 2019-052102 A | 4/2019 |
| WO | WO 2009/062399 A1 | 5/2009 |
| WO | WO 2013/086354 A1 | 6/2013 |
| WO | WO 2015/178343 A1 | 11/2015 |
| WO | WO 2016/210190 A1 | 12/2016 |
| WO | WO 2017/222016 A1 | 12/2017 |
| WO | WO 2019/176079 A1 | 9/2019 |

OTHER PUBLICATIONS

U.S. Appl. No. 16/567,895, filed Sep. 11, 2019, Ishihara et al.
Maier et al., "Biodegradable Lipids Enabling Rapidly Eliminated Lipid Nanoparticles for Systemic Deliver of RNAi Therapeutics", Molecular Therapy vol. 21, No. 8, Aug. 2013, 9 pages.
Jayaraman et al., "Maximizing the Potency of siRNA Lipid Nanoparticles for Hepatic Gene Silencing in Vivo", Angewandte Chemie, International Edition, vol. 51, 2012, pp. 8529-8533.
Michel et al., "Cationic Nanoliposomes Meet mRNA: Efficient Delivery of Modified mRNA Using Hemocompatible and Stable Vectors for Therapeutic Applications", Molecular Therapy: Nucleic Acids, 2017, 10 pages.
International Search Report dated Jun. 18, 2019 in PCT/JP2019/010681 filed on Mar. 14, 2019, 3 pages.

(Continued)

*Primary Examiner* — Kristin A Vajda
(74) *Attorney, Agent, or Firm* — Oblon, McClelland, Maier & Neustadt, L.L.P.

(57) ABSTRACT

The present embodiment provides a compound represented by the formula (1):

$$Q\text{-}CHR_2 \qquad (1)$$

(Q is a nitrogen-containing aliphatic group containing two or more tertiary nitrogens but no oxygen, and R is an aliphatic group containing a biodegradable group). From the compound in combination with other lipids such as a lipid capable of reducing aggregation, lipid particles can be formed. Further, the compound can be used for a pharmaceutical composition to deliver an activator into cells.

35 Claims, 6 Drawing Sheets

(56) References Cited

OTHER PUBLICATIONS

Luo et al., "Targeted delivery of pixantrone to neutrophils by poly (sialic acid)-p-octadecylamine conjugate modified liposomes with improved antitumor activity", International Journal of Pharmaceutics vol. 547, 2018, pp. 315-329.
Marques-Gallego et al., "Ligation Strategies for Targeting Liposomal Nanocarriers", Biomedical Research International, 2014, 13 pages.
Nogueira et al., "Design of liposomal formulations for cell targeting", Colloids and Surfaces B: Biointerfaces, vol. 136, 2015, pp. 514-526.

* cited by examiner

BIODEGRADABLE COMPOUND, LIPID PARTICLE, COMPOSITION COMPRISING LIPID PARTICLE, AND KIT

CROSS REFERENCE TO RELATED APPLICATIONS

This application is based upon and claims the benefit of priority from the prior International Patent Application PCT/JP2019/010681, filed on Mar. 14, 2019, the entire contents of which are incorporated herein by reference.

TECHNICAL FIELD

The present disclosure relates to a biodegradable compound having a structure decomposed in a cell, and also to lipid particles containing the compound. The disclosure further relates to a composition and a kit which are used for delivering an activator such as a nucleic acid.

BACKGROUND ART

Studies and researches have been made on liposomes for the purpose of various disease treatments. Liposomes are lipid-made minute capsules with nanometer-order sizes. They can enclose therein various compounds and the like and also are excellent in biocompatibility, and hence are ideal material for selectively delivering therapeutic agents or activators to the aimed parts in living bodies. For that use, large unilamellar liposomes (LUV: large unilamellar vesicles) having a mean particle size of 100 nm or more are generally employed and various substances have been developed for the membrane of them.

The liposomes can be made of a single lipid. In that case, for example, a phospholipid having a head part and a hydrophobic part connected thereto is adopted as the lipid, so that molecules thereof assemble to form membranes and thereby to produce the minute capsules capable of enclosing activators or the like. However, in order that the liposomes can have favorable properties, they are generally made of a lipid mixture. The mixture comprises a combination of, for example, lipids having excellent biodegradability, lipids inhibiting aggregation of the formed liposomes, lipids having an effect of inhibiting leakage of enclosed substances, and lipids having an effect of membrane fusion.

Those lipids are individually under research and development to further improve properties of the liposomes. For example, medical-use liposomes specialized for gene transfer are preferred to have high biodegradability, excellent biocompatibility, strong ability for gene transfer and low cytotoxicity, and accordingly lipids are preferably capable of forming those liposomes.

As the lipids described above, various compounds have been developed. However, living bodies to be treated may underlie various conditions and there are many diseases to be cured, and hence it is desired to increase kinds of lipids that can be selected according to the requirements. Further, there is a desire for lipids capable of forming liposomes having properties superior to those of conventional liposomes.

PRIOR ART DOCUMENTS

Patent Documents

[Patent document 1] Japanese Patent No. 5893611
[Patent document 2] Japanese Patent No. 6093710

DISCLOSURE OF INVENTION

Problem to be Solved by the Invention

In view of the above problem, the embodiment of the present disclosure provides a new compound serving as a lipid capable of forming liposomes, and also provides lipid particles, a composition and a kit using the compound.

Means for Solving Problem

The compound according to the embodiment is represented by the formula (1):

$$Q\text{-CHR}_2 \qquad (1)$$

wherein

Q is a nitrogen-containing aliphatic group containing two or more tertiary nitrogens but no oxygen, and each R is independently an aliphatic group of $C_{12}$ to $C_{24}$ provided that at least one R has, in the main chain or side chain thereof, a linking group $L^R$ selected from the group consisting of —C(=O)—O—, —O—C(=O)—, —O—C(=O)—O—, —S—C(=O)—, —C(=O)—S—, —C(=O)—NH— and —NH—C(=O)—.

Also, the lipid particles according to the embodiment are characterized by containing the above compound.

Further, the composition according to the embodiment is characterized by comprising the above lipid particles and a medium.

Furthermore, the kit according to the embodiment is characterized by comprising the above lipid particles and a composition containing an introducer that introduces the above lipid particles into cells.

DETAILED DESCRIPTION

Definitions

Figure 1:
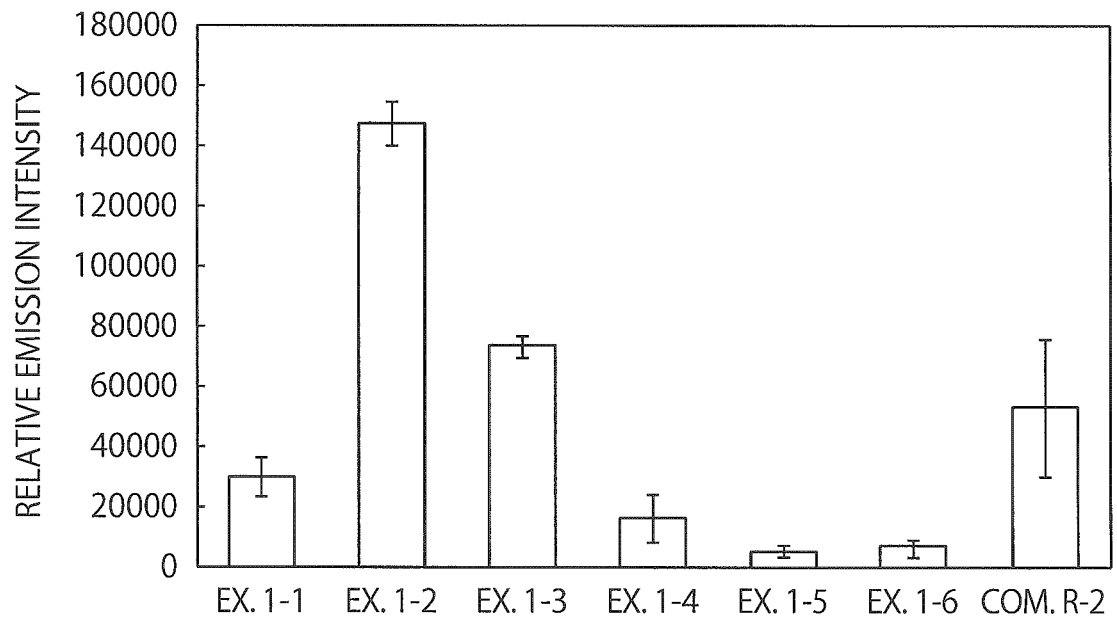
FIG. 1 is a graph showing enzyme activities when the lipid particles were applied to Jurkat cells in examples and a comparative example.

Unless otherwise specified in the present specification, when numerical ranges are indicated using "to", they include both endpoints, and units thereof are common. For example, "10 to 25 mol %" means 10 mol % or more and 25 mol % or less.

In the present specification, the descriptions such as "$C_x$-$C_y$" and "$C_x$" mean the number of carbons in the molecule or substituent. For example, the term "$C_1$-$C_6$ alkyl" means an alkyl having 1 or more and 6 or less carbons. Also, in the present specification, "halogenated alkyl" refers to an alkyl in which one or more hydrogens in the alkyl are replaced with halogen. For example, "fluoroaryl" refers to an aryl in which one or more hydrogens in the aryl are replaced with fluorine.

Unless otherwise stated in the present specification, the term "alkyl" means a monovalent group obtained by eliminating one hydrogen from an arbitrary carbon of alkane. The "alkyl" includes a linear or branched alkyl. In addition, "cycloalkyl" means an alkyl having a cyclic structure. Moreover, an alkyl having a cyclic structure which contains a linear or branched alkyl substituent is also referred to as a "cycloalkyl".

Further, the term "alkel" means a monovalent group obtained by eliminating one hydrogen from an arbitrary carbon of alkene.

Furthermore, "hydrocarbon group" means a monovalent or divalent or more valent group which includes carbon and hydrogen, and optionally oxygen or nitrogen. Also, "aliphatic group" means a hydrocarbon group having no aromatic ring, and the structure thereof may be a linear, branched or cyclic one. The structure may be a combination of them. Unless otherwise specified, the aliphatic group may have an unsaturated bond. Further, unless otherwise specified, the aliphatic group may contain a hetero atom, such as, nitrogen, oxygen, sulfur, selenium, fluorine, chlorine or bromine. In addition, the aliphatic group may be monovalent or multivalent. Still further, "aromatic hydrocarbon group" is a group containing an aromatic ring and may have, if necessary, an aliphatic hydrocarbon group as a substituent.

Furthermore, "tertiary nitrogen" means a nitrogen linking with three carbons, and accordingly it forms an electron-donating tertiary amine structure.

[Biodegradable Lipid Compound]

The compound according to the embodiment is a substance suitably serving as a lipid for forming liposomes. It has a biodegradable group in its hydrophobic part, and hence functions as a biodegradable lipid compound. Further, it does not have a cationic group in the head part, and hence is inhibited from binding with proteins and consequently shows low toxicity in cells when applied to living bodies. The liposomes formed by this lipid compound have such non-cationic surfaces as reduce cytotoxicity enough to increase efficiency of introducing activators such as nucleic acids into cells.

The lipid compound is represented by the formula (1):

$$Q\text{-}CHR_2 \tag{1}$$

Hereinafter, Q and R in the formula are often referred to as "head part" and "hydrophobic group", respectively. In the formula, Q is a nitrogen-containing aliphatic group containing two or more tertiary nitrogens but no oxygen, and each R is independently an aliphatic group of $C_{12}$ to $C_{24}$ provided that at least one R has, in the main chain or side chain thereof, a linking group $L^R$ selected from the group consisting of —C(=O)—O—, —O—C(=O)—, —O—C(=O)—O—, —S—C(=O)—, —C(=O)—S—, —C(=O)—NH— and —NH—C(=O)—.

One of the characteristics of the compound according to the embodiment is that the head part Q contains two or more tertiary nitrogens but no oxygen.

The head part may further contain another nitrogen that forms a non-substituted amino or quaternary ammonium as long as it does not impair the effect of the embodiment, but preferably does not contain any nitrogen other than the tertiary nitrogens. In addition, the head part Q contains no oxygen and hence does not have a structure of oxy, hydroxy, carboxy, alkoxy, carboxylato or the like. Further, the head part Q may contain an ionic group, but is preferably a neutral group having no polar group.

Some preferred examples of the Q part can be represented by the following formula (1-Q):

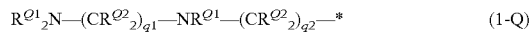

wherein
each $R^{Q1}$ is independently an alkyl,
each $R^{Q2}$ is independently hydrogen or an alkyl,
any two of $R^{Q1}$s and $R^{Q2}$s may link together to form a nitrogen-containing alicyclic ring,
q1 is an integer of 1 to 4,
q2 is an integer of 0 to 4, and
the mark * indicates the position bonding to —$CHR_2$.
Here, the alkyl is preferably an alkyl of $C_1$ to $C_3$.
In the above formula, any two of $R^{Q1}$s and $R^{Q2}$s can link together to form a nitrogen-containing alicyclic ring. There are no particular restriction on how many members the alicyclic ring has, but the ring is preferably 4- to 10-membered, more preferably 5- to 8-membered. Typical examples of the alicyclic ring include: piperidine, piperazine, pyrrolidine, imidazolidine, hexamethylene-imine, homopiperazine, and heptamethyleneimine.

Examples of the structure of the aforementioned Q part are as follows.

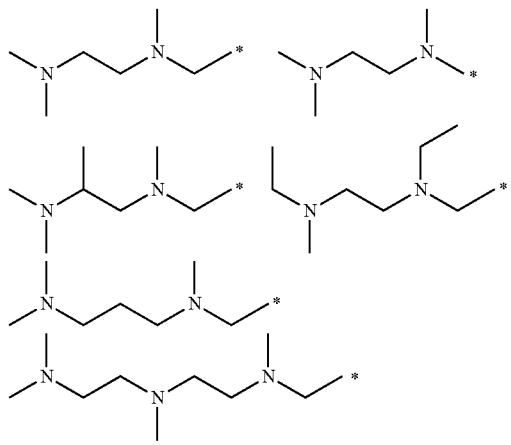

-continued

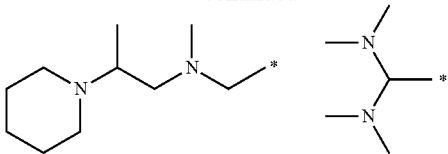

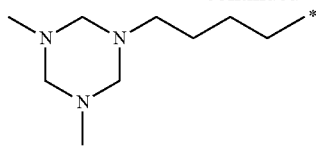

-continued (In each of the above formulas, * indicates the position bonding to —CHR$_2$.)

The compound according to the embodiment has —CHR$_2$, which connects with the head part. Here, R represents a hydrophobic group, and two Rs may be the same as or different from each other. The hydrophobic group generally contains a relatively long hydrocarbon chain. In the —CHR$_2$ moiety, there is a linking group containing carboxylato or the like in its part. Specifically, the —CHR$_2$ moiety has a linking group selected from the group consisting of —C(=O)—O—, —O—C(=O)—, —O—C(=O)—O—, —S—C(=O)—, —C(=O)—S—, —C(=O)—NH— and —NH—C(=O)—. Those linking groups function as biodegradable groups when the compound of the embodiment is used for liposomes.

Some preferred examples of the hydrophobic group R can be represented by the following formula (1-R):

$$-L^{R1}-C(=O)-O-L^{R2} \tag{1-R}$$

wherein
$L^{R1}$ and $L^{R2}$ are alkylene and alkenyl, respectively.

The $L^{R1}$ and $L^{R2}$ groups may have branched structures or cyclic structures. If they have branched structures, the number of side chains are preferably small. However, most preferably they have straight-chain structures.

Specifically, $L^{R1}$ and $L^{R2}$ are preferably represented by the following formulas (1-R1) and (1-R2), respectively:

$$-(CH_2)_{r1}- \tag{1-R1}$$

$$-CH_2-CH=CH-(CH_2)_{r2}-H \tag{1-R2}$$

wherein
r1 is an integer of 1 to 10, and
r2 is an integer of 1 to 10.

The integer r1 is preferably 4 to 8 and the longest molecular chain contained in the hydrophobic group R preferably consists of 8 or more atoms so that the hydrophobic group can show sufficient hydrophobicity.

The compound according to the embodiment comprises moieties having the above-described structures. Specifically, the compound of the embodiment preferably has a structure represented by one of the following formulas (1-01) to (1-21):

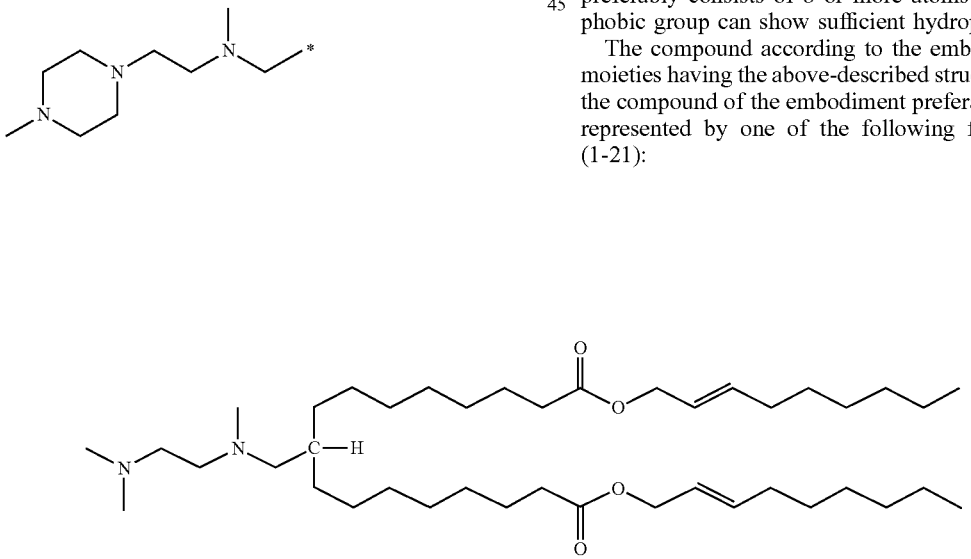

(1-01)

-continued
(1-02)
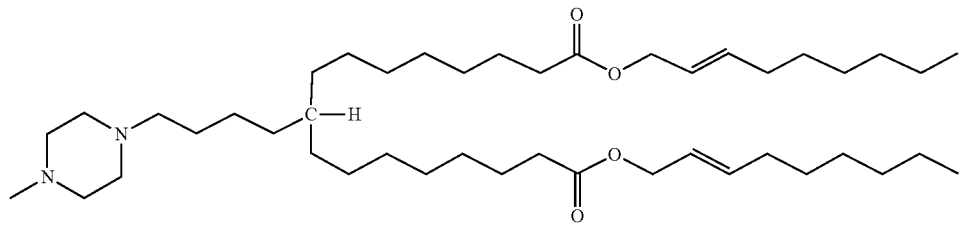
(1-03)
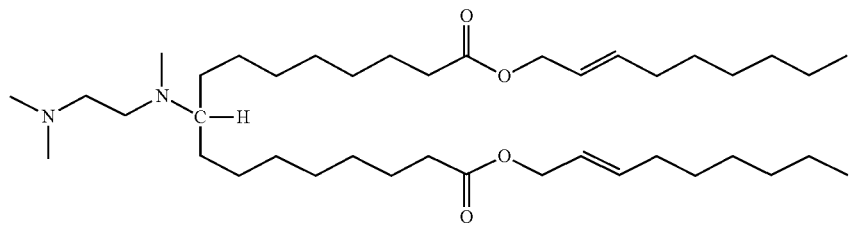
(1-04)
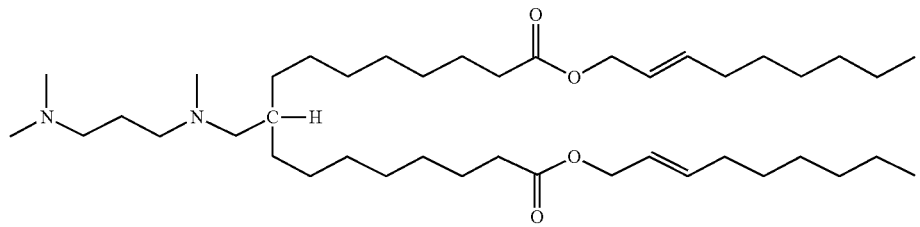
(1-05)
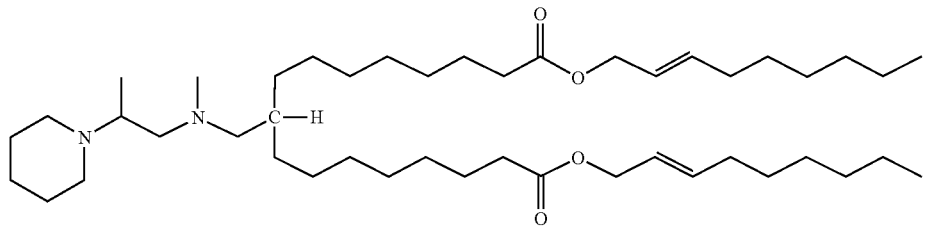
(1-06)
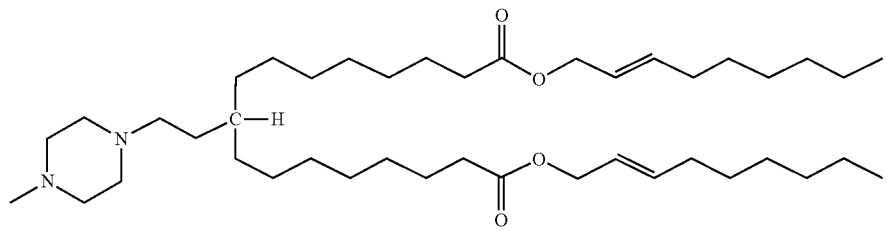
(1-07)
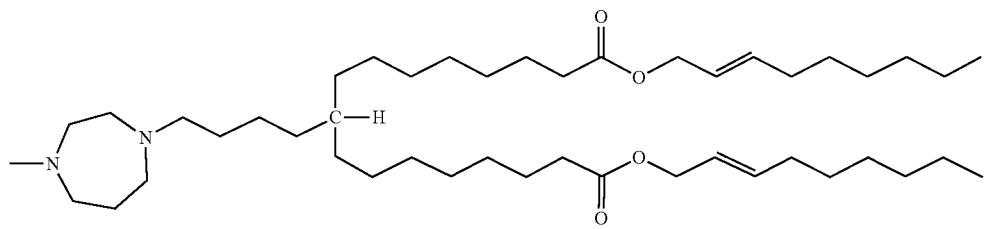
(1-08)
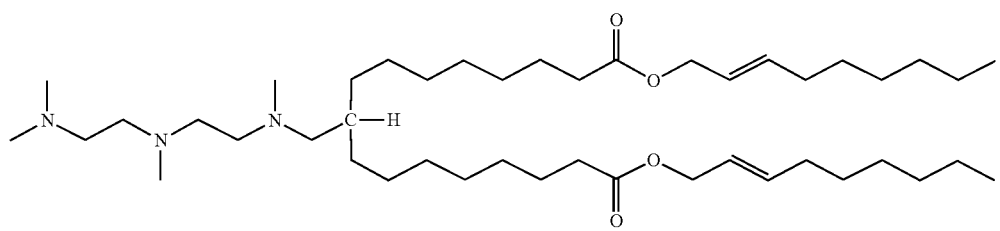

(1-09)
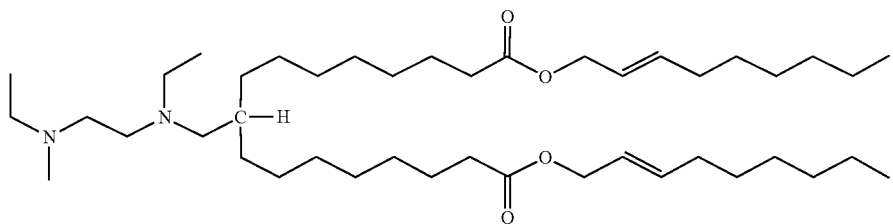
(1-10)
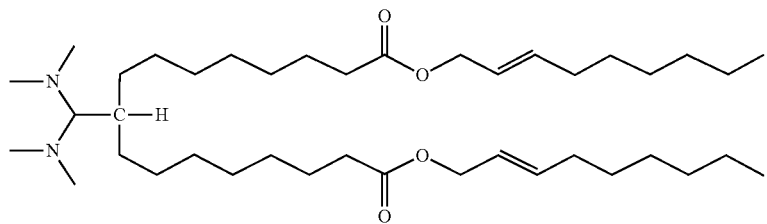
(1-11)
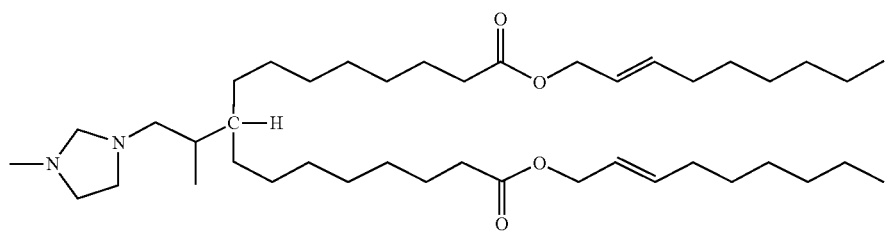
(1-12)
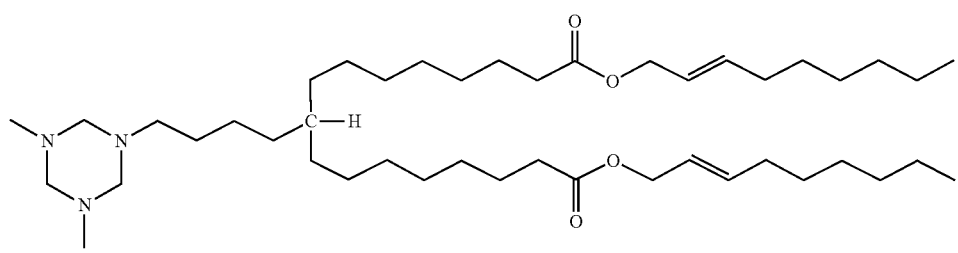
(1-13)
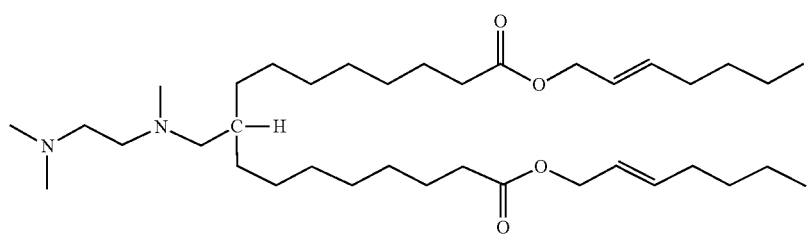
(1-14)
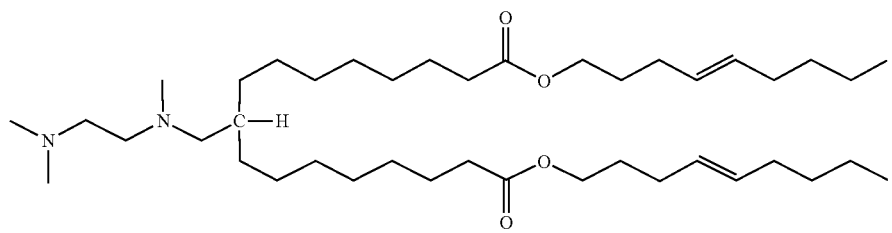

-continued
(1-15)
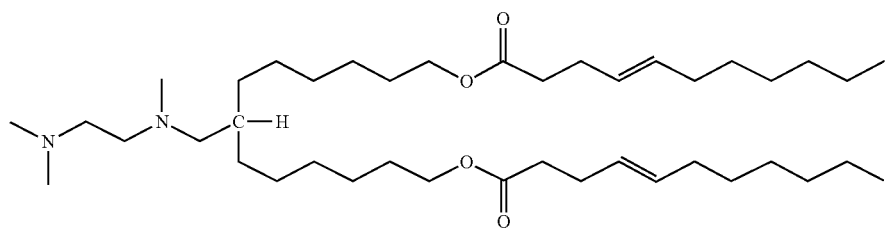
(1-16)
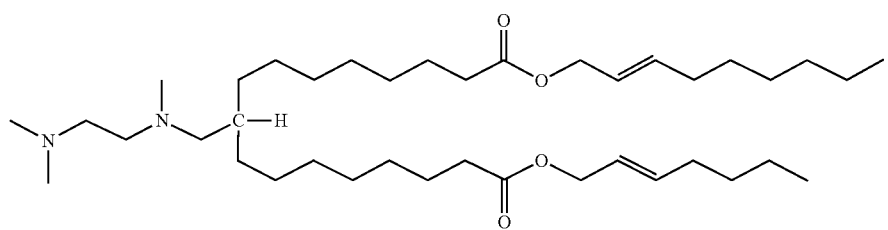
(1-17)
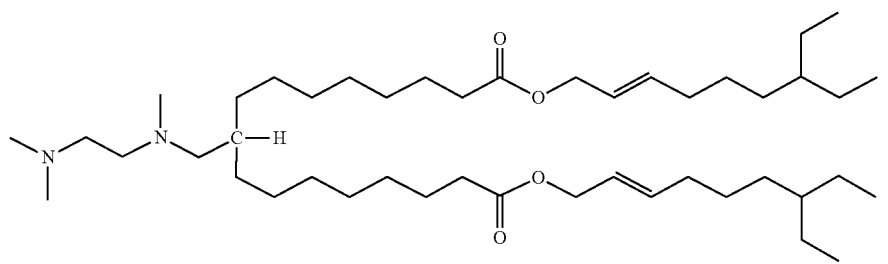
(1-18)
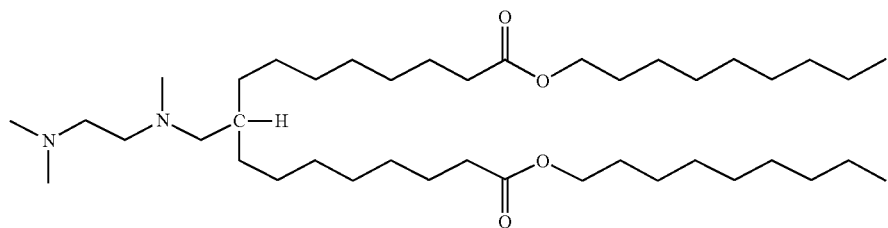
(1-19)
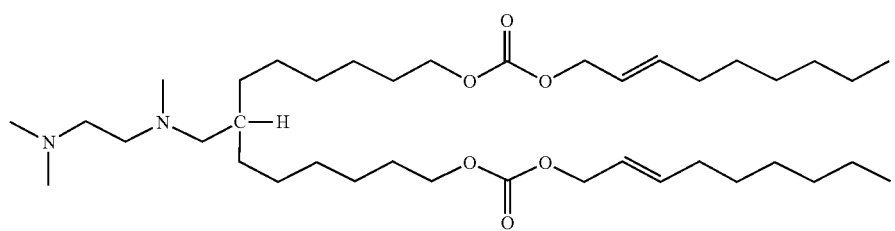
(1-20)
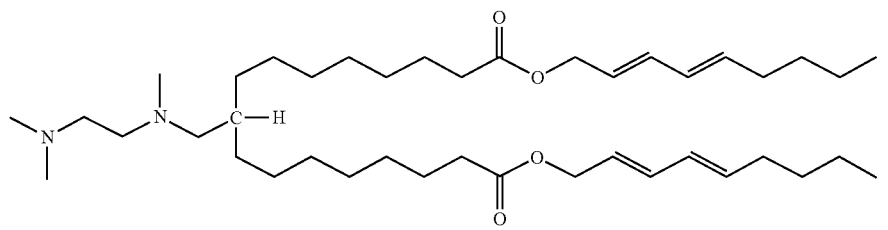

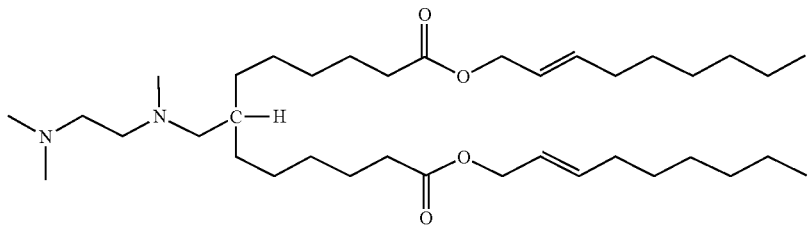
(1-21)

Among the above, the structures of (1-01) and (1-02) are particularly preferred because liposomes formed from them show excellent properties.

[Process for Producing the Compound]

The compound according to the embodiment can be produced in a desired manner. For example, the compounds (1-01) and (1-02) can be produced according to the steps shown by the following charts.

Synthesis of the Compound (1-01)

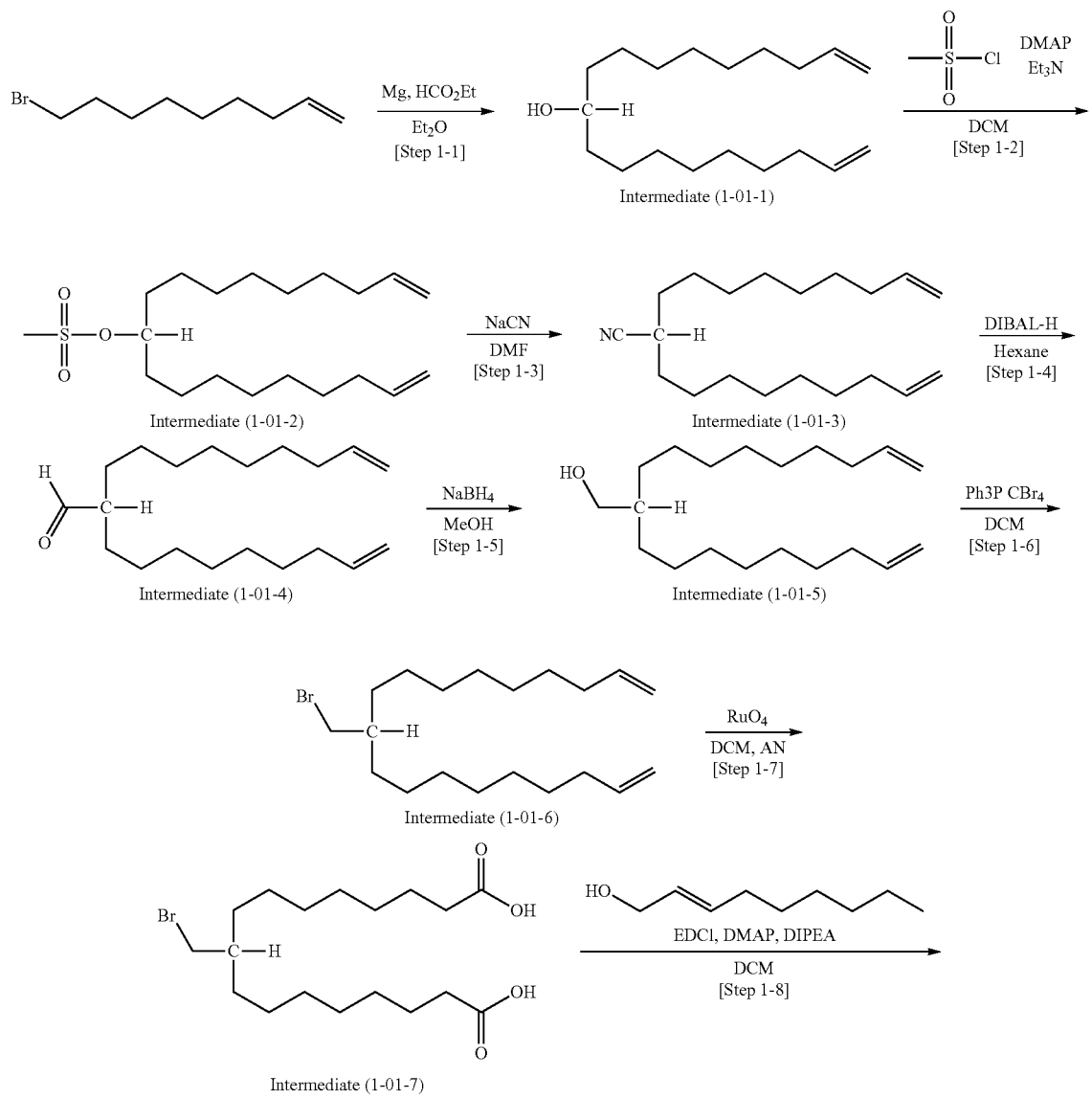

-continued
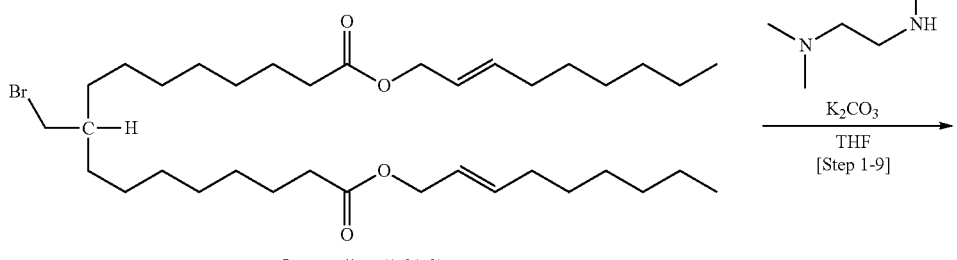
Intermediate (1-01-8)
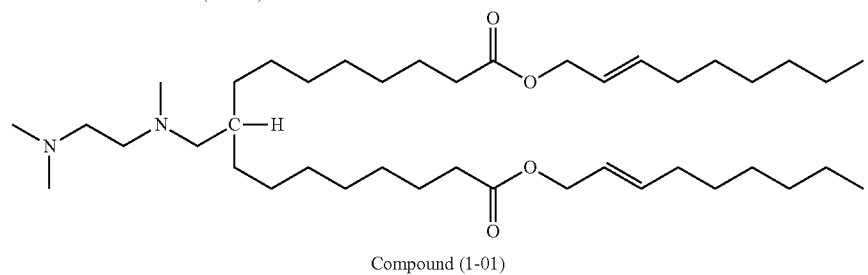
Compound (1-01)
Synthesis of the Compound (1-02) (1)
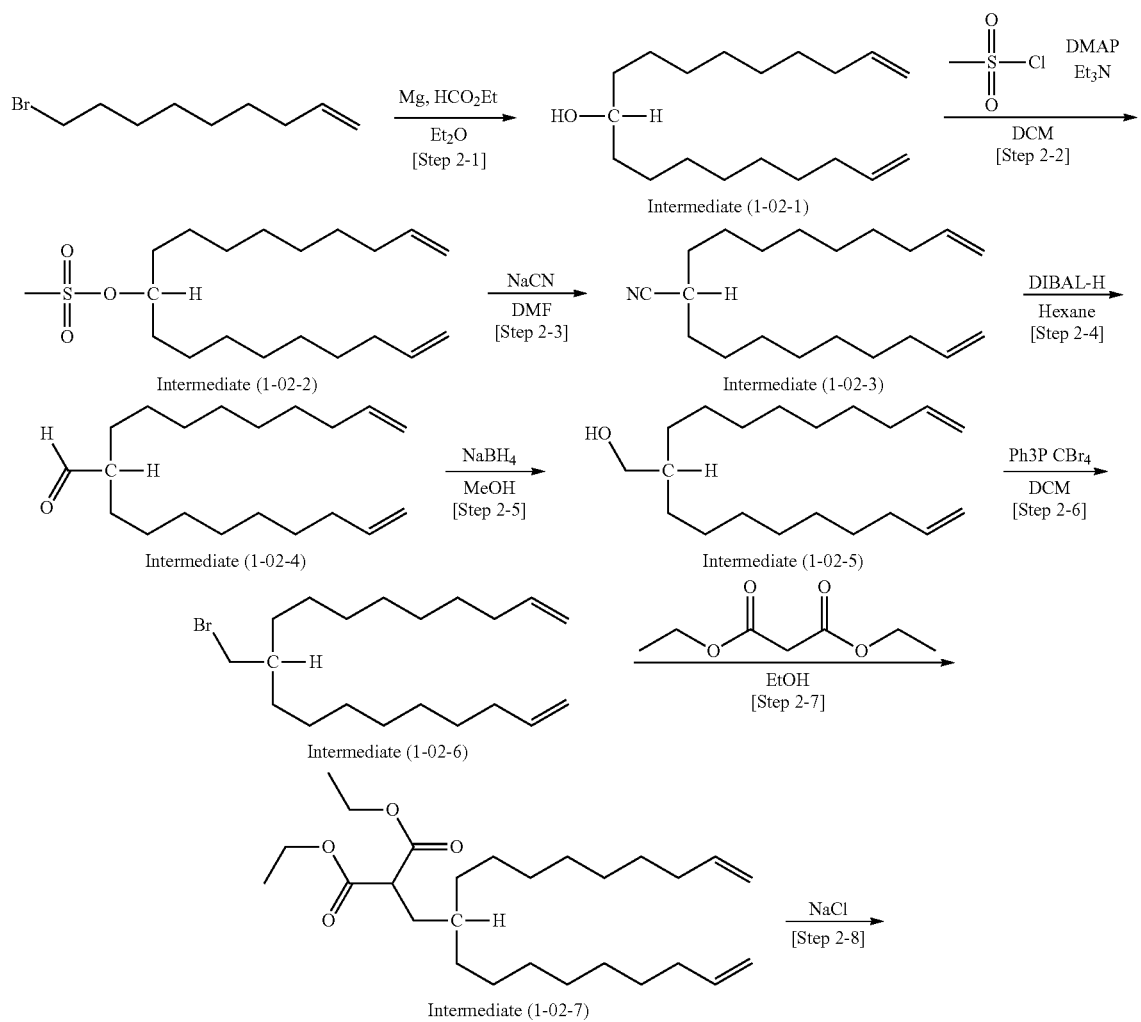

-continued
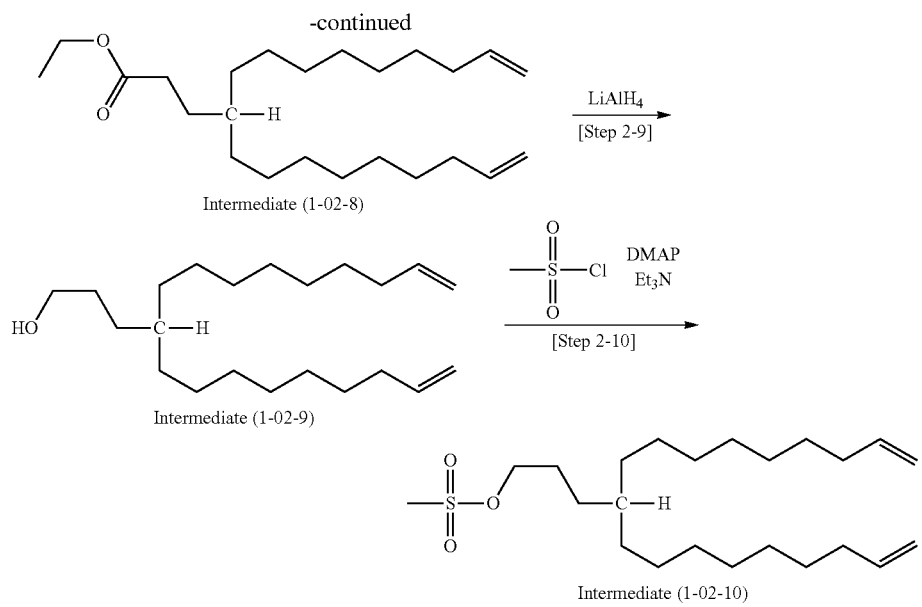
Synthesis of the Compound (1-01) (2)
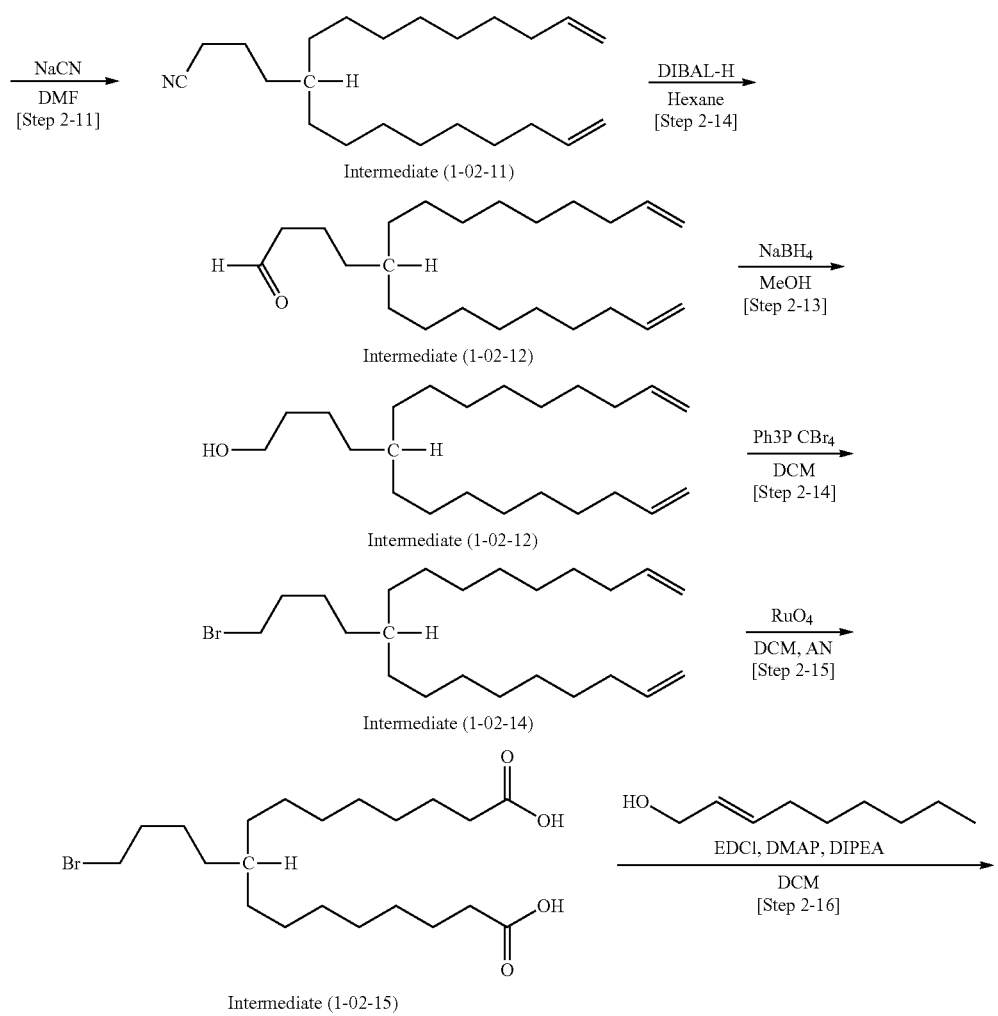

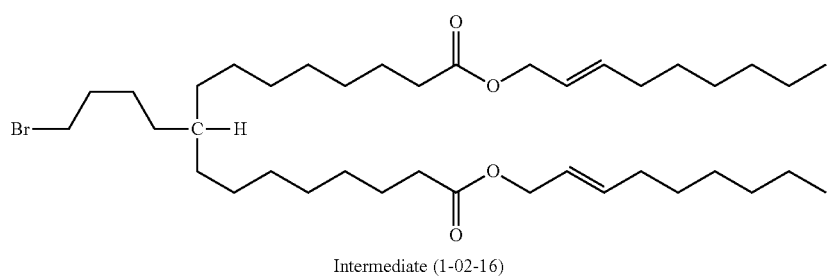
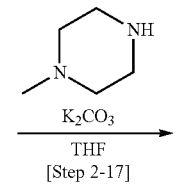

Intermediate (1-02-16)

[Step 2-17]

Compound (1-02)

[Lipid Particles]

The embodiment provides lipid particles. The lipid particles are typically liposomes, but not limited to them. For example, lipoplexes, which are liposomes complexed with nucleic acids or the like, are also included therein. The liposomes may be either unilamellar or multilamellar.

The lipid particles according the embodiment contain the compound represented by the above formula (1), and preferably further contain a lipid forming a membrane and a lipid capable of reducing aggregation.

As the lipid forming a membrane, any lipid can be adopted as long as it is generally used for liposomes. The lipid is preferably excellent in biodegradability.

Examples of the lipid forming a membrane include: diacyl phosphatidylcholine, diacyl phosphatidyl-ethanolamine, ceramide, sphingomyelin, dihydro-sphingomyelin, cephalin, and cerebroside. In the embodiment, the lipid forming a membrane is properly selected in consideration of sizes and stability of the aimed liposomes in living bodies. Among the above, diacyl phosphatidylcholine and diacyl phosphatidyl-ethanolamine are preferred. The acyl group contained in the lipid preferably has a hydrocarbon chain of 10 to 20 carbon atoms. The hydrocarbon chain may be either saturated or unsaturated.

As the lipid forming a membrane, various substances are known. Examples thereof include: 1,2-dioleoyl-sn-glycero-3-phosphoethanolamine (DOPE), 1,2-stearoyl-sn-glycero-3-phosphoethanolamine (DSPE), 1,2-dipalmitoyl-sn-glycero-3-phosphatidylcholine (DPPC), 1-palmitoyl-2-oleoyl-sn-glycero-3-phosphatidylcholine (POPC), 1,2-di-o-octadecyl-3-trimethylammoniumpropane (DOTMA), 1,2-dioleoyl-3-dimethylammoniumpropane (DODAP), 1,2-dimyristoyl-3-dimethylammoniumpropane (14:0 DAP), 1,2-dipalmitoyl-3-dimethylammoniumpropane (16:0 DAP), 1,2-distearoyl-3-dimethylammoniumpropane (18:0 DAP), N-(4-carboxybenzyl)-N, N-dimethyl-2,3-bis(oleoyloxy)-propane (DOBAQ), 1,2-dioleoyl-3-trimethylammoniumpropane (DOTAP), 1,2-dioleoyl-sn-glycero-3-phosphochlorin (DOPC), 1,2-dilinoleoyl-sn-glycero-3-phosphochlorin (DLPC), 1,2-dioleoyl-sn-glycero-3-phospho-L-serine (DOPS), and cholesterol. Among the above, DOPE, DOTAP and cholesterol are preferred, and combinations of DOPE with cholesterol, DOTAP with cholesterol, and DOPE with DOTAP and cholesterol are particularly preferred. Those lipids not only have a function of forming a membrane of liposomes but also can show an effect of membrane fusion.

The lipid capable of reducing aggregation used in the embodiment fulfills a function of reducing aggregation among the particles in preparation thereof. Various lipids having that function are known and any of them can be selected to use in the lipid particles of the embodiment. Examples thereof include: polyethylene glycol (PEG)-modified lipid, polyamide oligomer derived from ω-amino(oligoethylene glycol) alkanic acid monomer (U.S. Pat. No. 6,320,017), and mono-sialo ganglioside. More specifically, ATTA lipids such as ATTA8-DPSE disclosed in U.S. Pat. No. 6,320,017 and polyethylene glycol-lipid conjugates disclosed in U.S. Pat. Nos. 5,820,873, 5,534,499 and 5,885,613 are employable.

When the lipid particles are produced, the PEG-modified lipid can form anchoring lipid-moieties on the surface of the particles. Examples of the PEG-modified lipid include: PEG-modified phosphatidyl-ethanolamine, PEG-modified phosphatidic acid, PEG-ceramide conjugates (e.g., C14 PEG-Cer or C20 PEG-Cer disclosed in Japanese Patent No. 3920330), PEG-modified dialkylamine, PEG-modified 1,2-diacyl-oxypropane-3-amine, PEG-modified diacylglycerol (e.g., 1,2-dimyristoyl-sn-glycerol-methoxypolyethyenegly-col: PEG-DMG), and PEG-modified dialkylglycerol. Among them, PEG-modified diacylglycerol and PEG-modified dialkylglycerol are particularly preferred.

When bulky modifying groups such as PEG are bound to the surfaces of the lipid particles, the bonds between the modifying groups and the lipid particles have influence on stability of the lipid particles or liposomes. For example, U.S. Pat. No. 5,820,873 describes that the stability of lipid particles depends on such characteristics of the PEG modifying lipid as the length and saturation degree of the acyl chain and the size of the bulky head group in the modifying lipid. Accordingly, those characteristics can be controlled so as to obtain the aimed lipid particles. For example, it is possible to select a PEG modifying lipid having short modifying groups so that the lipid particles may disappear in a short time, and it is also possible to select one having long modifying groups so that the lipid particles may stay in plasma for a long time. As a result, it is often possible to improve delivery of lipid particles to the target tissue.

The lipid particles can furthermore contain other lipids, which can be freely selected from generally used ones. For example, in order to control the toxicity, relatively low-toxic lipids can be incorporated. Further, it is also possible to incorporate a lipid having a particular structure so as to introduce functional groups for combining the lipid particles with ligands.

Moreover, when the lipid particles are adopted as liposomes, they can contain a sterol, such as cholesterol, as a lipid for inhibiting leakage of the enclosed substance. It is further possible to couple the lipid particles with a target agent. In that case, the coupling method can be freely selected from known methods.

More preferably, the lipid particles according the embodiment further contain a compound represented by the formula (2):

$$P—[X—W—Y—W'—Z]_2 \quad (2)$$

wherein

P is an alkyleneoxy having one or more ether bonds in the main chain, each X is independently a divalent linking group having a tertiary amine structure, each W is independently a $C_1$ to $C_6$ alkylene, each Y is independently a divalent linking group selected from the group consisting of single bond, ether bond, carboxylic ester bond, thiocarboxylic ester bond, thioester bond, amide bond, carbamate bond, and urea bond, each W' is independently a single bond or a $C_1$ to $C_6$ alkylene, and each Z is independently a liposoluble vitamin residue, a sterol residue, or a $C_{12}$ to $C_{22}$ aliphatic hydrocarbon group; provided that the structure further contains at least one biodegradable group selected from the group consisting of carboxylic ester bond, thiocarboxylic ester bond, dithiocarboxylic bond, amide bond, carbamate bond, carboxydioxy bond, and urea bond.

The compound represented by the formula (2) is also a biodegradable lipid compound. When combined with the compound of the formula (2), that of the formula (1) can show a new function. For example, if the compound of the formula (2) is used for liposomes, the amount of nucleic acid enclosed therein can be improved. Accordingly, if the compounds of the formulas (1) and (2) are used for liposomes in combination, it becomes easy to apply the liposomes to gene therapy, nucleic acid medicine and genomic diagnosis.

One of the characteristics of the compound represented by the formula (2) is that P in the formula (2) has an ether bond. In other words, P comprises at least one oxygen and the oxygen connects to two carbons. There are no particular restrictions on the number of oxygens contained in P, but preferably one or two oxygens are contained. Also, there are no particular restrictions on the number of carbons contained in P, but the hydrocarbon chain included in P preferably has 1 to 3 carbons and the total number of carbons in P is preferably 3 to 8. Examples of the preferred P are as follows:

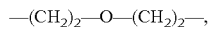

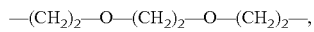

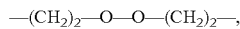

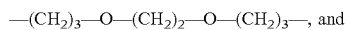

Because of the above structure, the compound molecule can be in a relatively free conformation. When the compound is used for producing liposomes, oxygens in the ether bonds form hydrogen bonds with incorporated nucleic acids or the like and, as a result, the enclosed amount thereof is increased.

Each X is a divalent linking group having a tertiary amine structure, and is preferably selected from the group consisting of methylimino, 1,2-pyrrolidinediyl and 1,3-pyrrolidinediyl. When the compound is used for producing liposomes, the tertiary amine structure provides high cell-membrane permeability.

In the formula (2), the W—Y—W'—Z moiety is a hydrophobic part. The hydrophobic part contains a biodegradable group, which is selected from the group consisting of carboxylic ester bond (—C(=O)—O—), thiocarboxylic ester bond (—C(=O)—S—), dithiocarboxylic ester bond (—C(=S)—S—), amide bond (—C(=O)—NH—), carbamate bond (—NH—C(=O)—O—), carboxydioxy bond (—O—C(=O)—O—), and urea bond (—NH—C(=O)—NH—).

The biodegradable group may be contained in the structure as Y, but it may be in Z. Specifically, when Z is a group derived from a liposoluble vitamin or a sterol, the group may contain a carboxylic ester group or the like. The biodegradable group may be contained in both of Y and Z, or either of them may contain two or more biodegradable groups.

Both of Y and W' are divalent groups linking W to Z.

Each Y is a divalent linking group selected from the group consisting of single bond, ether bond, carboxylic ester bond, thiocarboxylic ester bond, thioester bond, amide bond, carbamate bond, and urea bond. Each W' is a single bond or a $C_1$ to $C_6$ alkylene.

They need not comprise atoms and may be single bonds. However, when Z does not contain a biodegradable group, Y contains a biodegradable group.

Each Z is a liposoluble vitamin residue, a sterol residue, or a $C_{12}$ to $C_{22}$ aliphatic hydrocarbon group. Among them, a liposoluble vitamin residue and a sterol residue are preferred, and a liposoluble vitamin residue is more preferred.

The liposoluble vitamin residue is a group derived from a liposoluble vitamin. Examples of the liposoluble vitamin include: retinol, retinal, ergosterol, 7-dehydrocholesterol, calciferol, cholecalciferol, dihydroergocalciferol, dihydrotachysterol, tocopherol, and tocotrienol. Those liposoluble vitamins have hydroxy groups at their terminals. The liposoluble vitamin residue is, for example, a group formed by eliminating a hydrogen atom from one of those hydroxy groups. The residue may be a group derived from a liposoluble vitamin derivative. The liposoluble vitamin derivative is a compound in which hydroxy in a liposoluble vitamin is replaced with thiohydroxy, carboxy, thiocarboxy or dithiocarboxy. The liposoluble vitamin residue has —S—, —C(=O)—O—, —C(=O)—S— or —C(=S)—S— at the terminal. It is particularly preferred for the liposoluble vitamin residue to be a group derived from retinol (vitamin A), tocopherol (vitamin E) or carboxylic acid derivatives thereof.

The sterol residue is a group derived from a sterol. Examples of the sterol include cholesterol, stigmasterol, β-sitosterol, lanosterol, and ergosterol. The sterol residue is, for example, a group formed by eliminating a hydrogen from the hydroxy in those sterols. The sterol residue may have the same terminal group as the above-described group derived from a liposoluble vitamin derivative. It is particularly preferred for the sterol residue to be a group derived from sterol, cholesterol, or carboxylic acid derivatives thereof.

The C$_{12}$ to C$_{22}$ aliphatic hydrocarbon group may be either linear or branched, and further may have a cyclic structure. The aliphatic hydrocarbon group may have unsaturated bonds. In that case, it generally has 6 or less, preferably 3 or less unsaturated bonds. The aliphatic hydrocarbon group contains preferably 12 to 18, more preferably 13 to 17 carbon atoms.

Among the above groups serving as Z, preferred are groups having UV-absorbing structures. Specifically, it is preferred to have a cyclohexane structure. If the compound contains a UV-absorbing structure, it becomes possible to reduce light-deterioration of lipid particles containing the compound as an ingredient and further, when the lipid particles need to be subjected to behavior analysis, the analysis can be easily carried out.

The compound of the formula (2) contains two [X—W—Y—W'—Z] units. Those Xs, Ws, Ys, W's and Zs are individually independent, and they may be the same as or different from each other. However, they are preferably the same so that the compound may have an objective structure.

Each part of the compound according to the embodiment has the structure described above. The compound of the embodiment preferably has a structure represented by one of the following formulas (2-01) to (2-12).

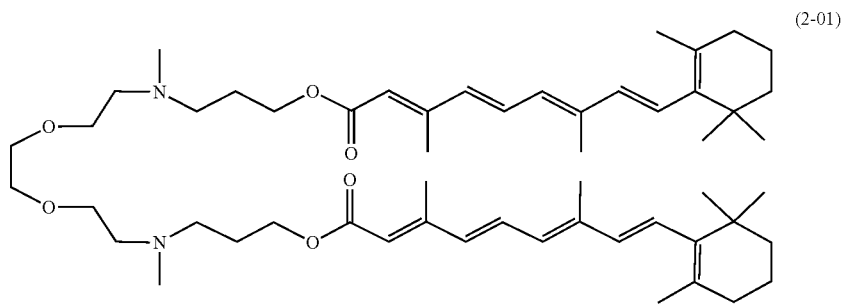

(2-01)

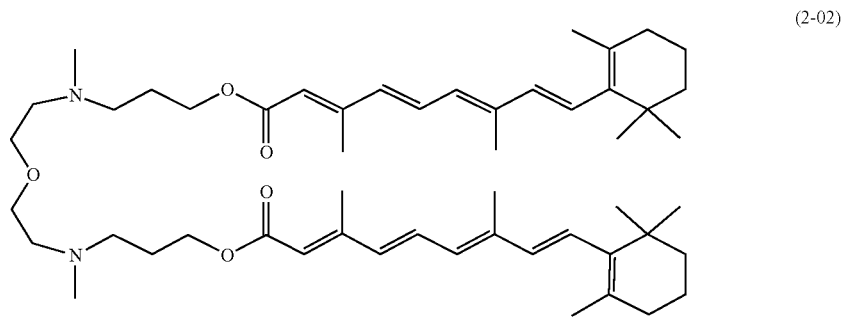

(2-02)

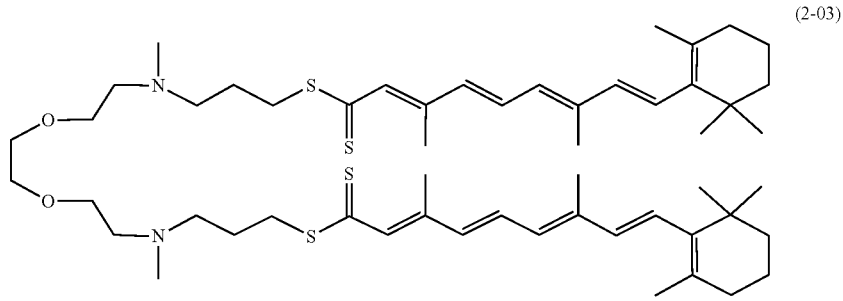

(2-03)

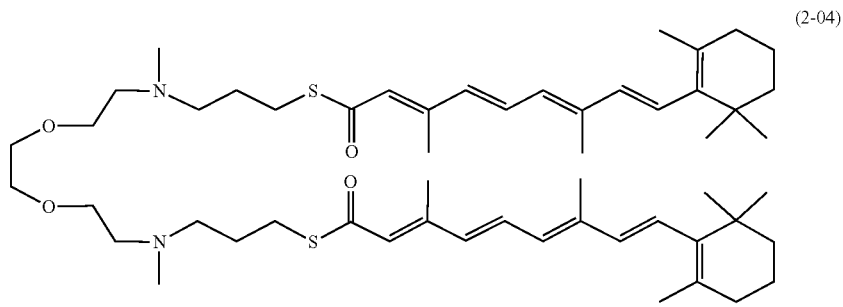

(2-04)

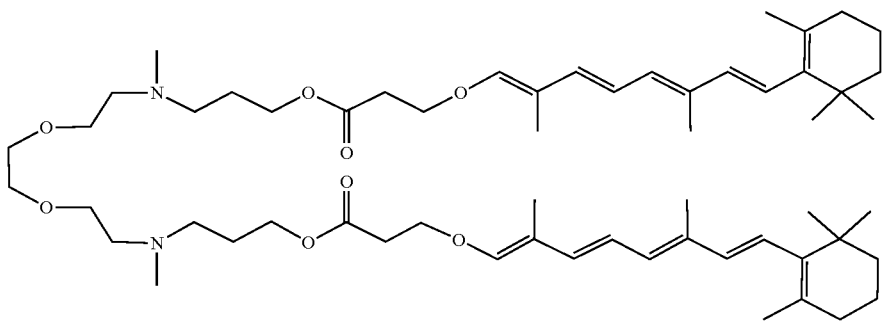
(2-05)
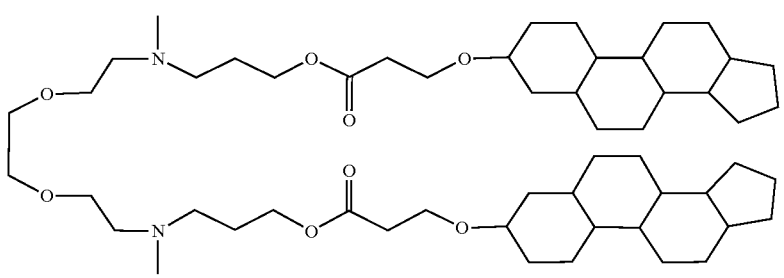
(2-06)
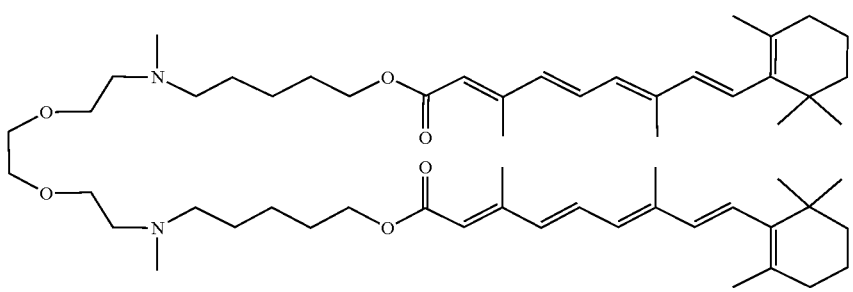
(2-07)
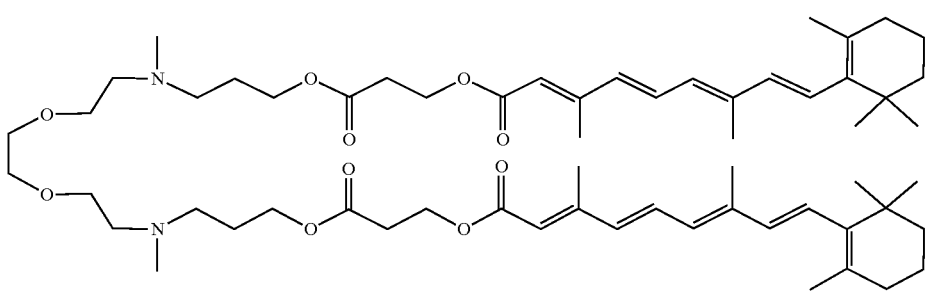
(2-08)
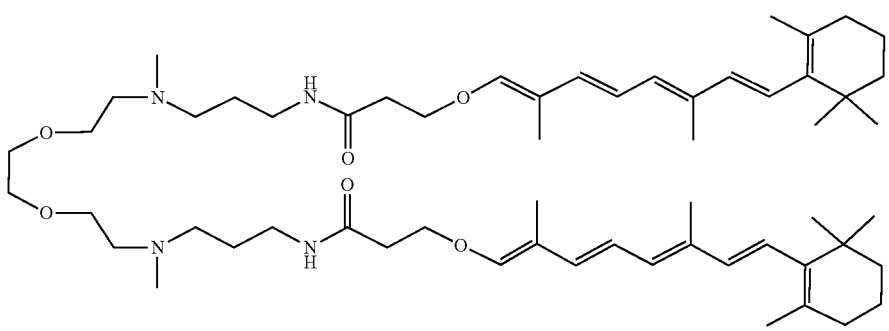
(2-09)

-continued
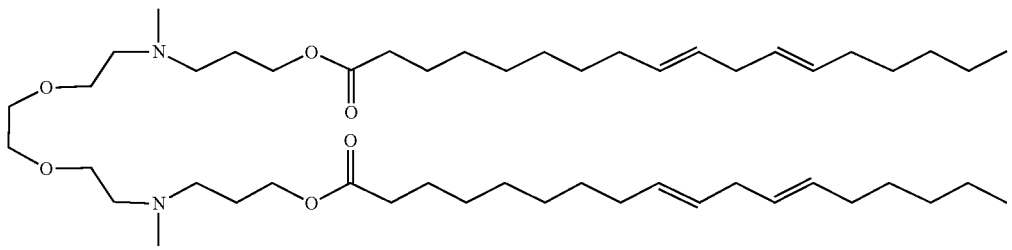
(2-10)
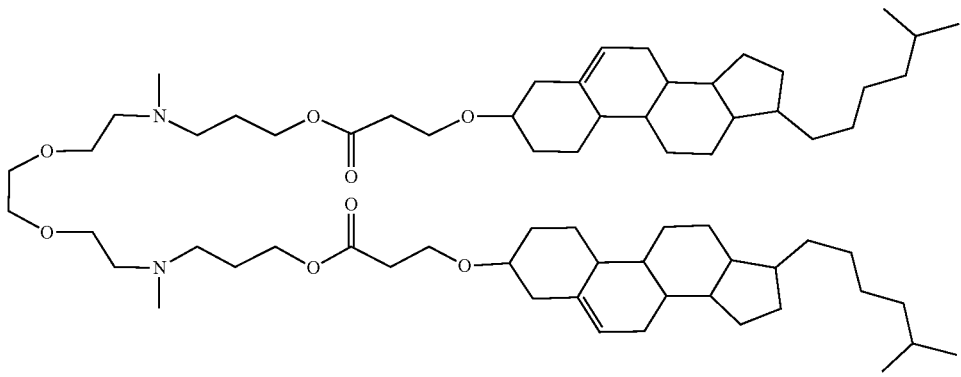
(2-11)
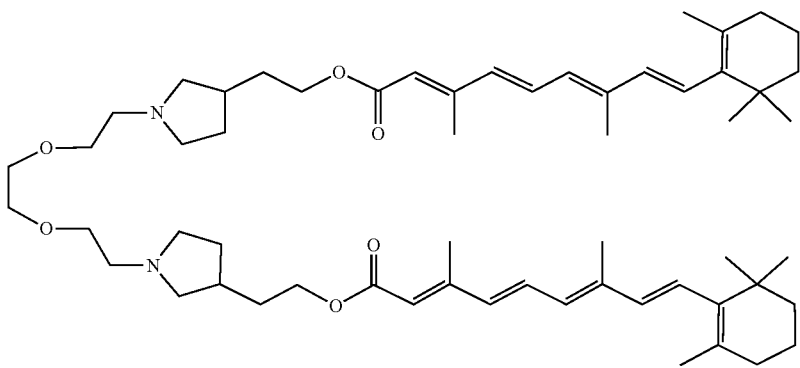
(2-12)
Among the above, the structures of (2-01) to (2-04) are particularly preferred because liposomes formed from combinations of them with the compound of the formula (1) show excellent properties.
The compound of the formula (2) can be produced, for example, according to the steps shown by the following chart.
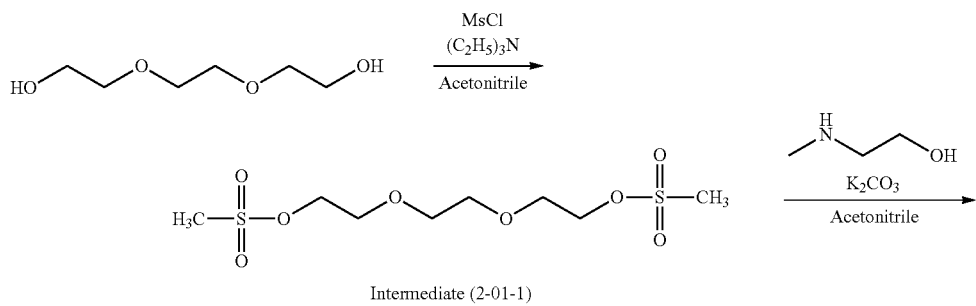
Intermediate (2-01-1)

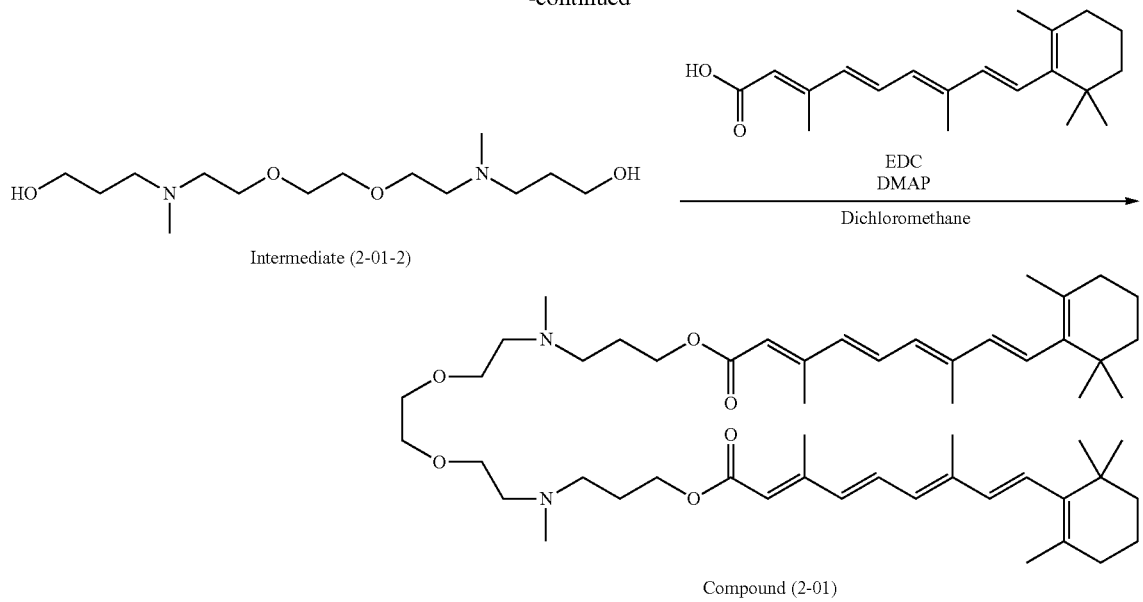

The lipids described above are combined to produce the lipid particles, and the blending ratio thereof are controlled according to the purpose and hence not particularly limited. However, the amounts of the lipids are generally as follows based on the total number of moles of the lipids used for the lipid particles: the lipid compounds represented by the formulas (1) and (2): 25 to 75 mol % in total, the lipid forming a membrane: 25 to 75 mol %, and the lipid capable of reducing aggregation: 1 to 10 mol %. Further, the amounts preferred are as follows: the lipid compounds represented by the formulas (1) and (2): 30 to 60 mol % in total, the lipid forming a membrane: 30 to 65 mol %, and the lipid capable of reducing aggregation: 1 to 10 mol %, for example, 2.5 mol %. Here, it should be noted that the balance between the compound of the formula (1) and the membrane-forming lipid is important and the introduction of the activator cannot be enhanced by only either one of them. Accordingly, the blending ratio between the compound of the formula (1) or (2) and the membrane-forming lipid is preferably 1:0.5 to 1:3, more 1:0.75 to 1:2.1 based on the number of moles.

Here, the "lipid forming a membrane or membrane-forming lipid" excludes the compound of the formula (1) or (2) although the compounds represented by the formulas (1) and (2) are both capable of functioning as a lipid forming a membrane.

The lipid particles of the embodiment can still further contain an activator. In the embodiment, "activator" means a substance that gives a specific effect to cells, tissues, organs or specimens. The specific effect may be biological, physiological or cosmetic one. The lipid particles of the embodiment makes it possible to deliver various activators to the aimed parts in living bodies. The activator may be enclosed in the lipid particles, may be attached on the outer or inner surface thereof, or may be placed inside of the lipid layer.

Typical examples of the activator are nucleic acids. For example, the activator is selected from the group consisting of plasmid, oligonucleotide, polynucleotide, small interfering RNA (siRNA), microRNA (miRNA), DNA, aptamer, and ribozyme. In addition, it is also possible to adopt antisense oligonucleotide, antago-mir, aDNA, plasmid, ribosomal RNA (rRNA), transfer RNA (tRNA), small nuclear RNA (snRNA), or mRNA. Further, it is also possible to adopt a combination of different kinds of DNAs or RNAs.

As the miRNA, a miRNA in which 17 to 25 nucleotide units are linked can be adopted. In a preferred embodied case, the nucleic acid is an oligonucleotide in which 15 to 50 or 20 to 30 nucleotide units are linked. The siRNA can, for example, comprise 16 to 30 nucleotide units and have a double-stranded region. In another embodied case, the nucleic acid is immune stimulating oligonucleotide, decoy oligonucleotide, super mir, miRNA mimic, or miRNA inhibitor. Here, "super mir" means a polymer or oligomer which is derived from single-, double- or partly double strands of RNA, DNA, both thereof or denatured one thereof, which has substantially the same nucleotide sequence as miRNA and which is antisense to the target. The "miRNA mimic" here means a group of molecules usable for the purpose of imitating the gene silencing ability of one or more miRNAs. Accordingly, the term "miRNA mimic" indicates a synthesized non-coding RNA capable of entering RNAi pathways and of controlling gene expression. (This means that miRNA mimic cannot be obtained by purification of substances collected from sources of endogenous RNA.)

When nucleic acids are used in combination with the lipid particles, the form thereof is not particularly restricted. For example, they may be single-strand DNAs or RNAs, double-strand DNAs or RNAs, or DNA-RNA hybrids. Examples of the double-strand RNA include siRNA. Examples of the single-strand nucleic acid include antisense oligonucleotide, ribozyme, miRNA, and triplehelix-forming oligonucleotide.

If containing a nucleic acid, the lipid particles of the embodiment can further contain a compound combinable with the nucleic acid. The compound is, for example, a basic protein or a basic peptide. Preferred examples thereof include protamine, histone, and salts thereof. Specifically, for example, when combined with histone or salts thereof, a nucleic acid molecule is folded therein. When combined with protamine or salts thereof, a nucleic acid molecule is rolled therein. Accordingly, those compounds are effective in enclosing the nucleic acid into the lipid particles.

The lipid particles of the embodiment can furthermore contain a compound controlling expression of the nucleic acid in cells. This compound is preferably incorporated because expression of nucleic acid in cells can be controlled so that cells to which liposomes are delivered may be visualized or led to cell death. Examples of the compound include retinoic acid, cyclic adenosine monophosphoric acid (cAMP), and ascorbic acid.

In addition, the lipid particles according to the embodiment may still further contain lipoprotein, apolipoprotein or the like.

As the activator, other therapeutic agents can be employed. Examples of the therapeutic agents include: peptides, polypeptides, cytokines, growth factors, apoptosis factors, differentiation inducers, cell surface receptors and ligands thereof, and hormones. Specifically, the therapeutic agents are, for example, anti-inflammatory compounds, antidepressants, stimulants, analgesics, antibiotics, contraceptives, antipyretics, vasodilators, angiogenesis inhibitors, cytovascular agents, signal transduction inhibitors, cardiovascular drugs, tumor drugs, hormones or steroids.

When used in combination with the lipid particles, the activator is preferably introduced into the particles at a high introduction rate. Also, cell death is preferably seldom caused by cytotoxicity depending on properties of the lipids. However, when nucleic acids are introduced by use of known lipid particles, the introduction rate is generally low and cell death is often caused by cytotoxicity. In contrast, if the lipid particles of the embodiment are adopted, the introduction rate of nucleic acids can be enhanced and the cell death can be reduced. Specifically, when known lipid particles are employed, the introduction rate is about 10% and the cell death is extrapolated to be 60 to 70%. On the other hand, when the lipid particles of the embodiment are employed, the introduction rate and the cell death are improved to be 70% or more and 30% or less, respectively.

The lipid particles of the embodiment can be produced in desired sizes according to the purposes. However, when employed for medical use, the lipid particles are generally in the form of nano-order size particles. Specifically, the lipid particles according to the embodiment have a mean particle size of generally 50 to 300 nm, preferably 50 to 200 nm. The size of the lipid particles can be controlled in any manner. For example, the particles can be subjected to ultrasonic treatment so as to reduce the sizes. Further, for the purpose of sizing the lipid particles, it is also possible to make the particles permeate through a polycarbonate or ceramic membrane. Here, in the present embodiment, the mean size of the lipid particles can be measured, for example, with a Zetasizer according to dynamic light scattering method.

The lipid particles of the embodiment has an in-vivo half-life ($t_{1/2}$) of generally less than 3 hours, preferably less than 2 hours, more preferably less than 1 hour. Here, "in-vivo half-life" means a half-life in, for example, the liver, the spleen or the plasma. Since the lipid is made of the compound of the formula (1) having a biodegradable group, the lipid particles of the embodiment has, for example, less than 10% as short a half-life as particles of lipids having no biodegradable group.

[Process for Producing the Lipid Particles]

The lipid particles according to the embodiment can be produced in any known manner. Examples of known methods for producing lipid particles or liposomes include Bangham method, organic solvent extraction method, surfactant removal method, and freeze-thaw method. Those may be adopted. However, in another way, for example, the compound represented by the formula (1), the lipid forming a membrane and the lipid capable of reducing aggregation are added in an organic solvent such as an alcohol, and then an aqueous buffer is added therein so that the lipid particles can spontaneously form. In this process, the activator can be introduced into the lipid particles if incorporated in the aqueous buffer.

[Application of Lipid Particles]

The lipid particles of the embodiment can be employed for delivering activators to cells. In particular, delivery to cells of activators such as nucleic acids is often adopted in various fields, for example, in genetic engineering, in production of recombinant proteins, and in medical technologies known as gene therapy and cytologic diagnosis. In an embodied case, there is provided a composition which can be used for delivering activators to cells and which is characterized by comprising the lipid particles of the embodiment and a medium. In another embodied case, there is also provided lipid particles of the embodiment for delivering activators to cells. In still another embodied case, there is still also provided a method by which activators can be delivered to cells and in which the lipid particles of the embodiment containing the activators are brought into contact with the cells (for example, the lipid particles are administered to the subject). In yet another embodied case, there is further provided a use of the lipid particles described in one of claims 9 to 22 for delivering activators to cells. In an embodied case, the above lipid particles contain both the compounds of the formulas (1) and (2) and preferably the mole ratio of the content of the compound of the formula (2) to that of the compound of the formula (1) is less than 1. The above cells are tumor cells in an embodied case. The above subject is preferably an animal, more preferably a mammal, most preferably a human that needs the treatment. Those described above are explained below in more detail.

[Composition]

The lipid particles according to the embodiment can be used in the form of a composition. For example, the composition comprises the lipid particles of the embodiment and a medium. That composition is applicable to medical use.

The medium can be optionally selected from known ones, and examples thereof include water, sodium chloride solution such as physiological saline, aqueous glycine solution, and buffer solution. In addition to those media, glycoproteins such as albumin, lipoproteins, apolipoproteins and globulin can be incorporated therein for the purpose of improving the stability.

The composition of the embodiment can be prepared in a standard manner. As the medium, physiological saline is normally adopted. When sodium chloride solution or other salt-containing medium is used in the composition, that medium is preferably added after the lipid particles are formed. Accordingly, in a normal manner, first the lipid particles and the activator such as a nucleic acid are combined and thereafter the obtained composition is then diluted with a pharmaceutically acceptable medium such as physiological saline.

The composition according to the embodiment can contain an auxiliary ingredient, if necessary. For example, when prepared for medical use, the composition can contain a pharmaceutically acceptable auxiliary ingredient, such as, pH adjuster, buffer agent or tonicity modifier, so as to be suited to physiological conditions. Examples of the auxiliary ingredient having that function include: sodium acetate, sodium lactate, sodium chloride, potassium chloride, calcium chloride and hydroxyethylpiperazineethanesulfonic acid (HEPES). The composition of the embodiment can further contain a lipid-protective agent for improving storage stability. The protective agent is, for example, a lipophilic free-radical quencher such as α-tocopherol, which prevents damage by free radicals; or a water-soluble chelator such as ferrioxamine, which prevents peroxidative damage of the lipid.

Further, the aforementioned activator can be added to the composition. The activator may be the same as or different from that combined with the lipid particles. Furthermore, the compound combinable with a nucleic acid and/or the compound controlling expression of nucleic acid can be added to the composition.

There are no particular restrictions on the amount of the lipid particles contained in the composition, but the amount thereof is generally 0.01 to 30 mass %, preferably 0.05 to 10 mass %. The concentration of the lipid particles can be properly selected according to the purpose.

The composition of the embodiment can be sterilized in known manners. The sterilized composition can be packaged as a pharmaceutical product capable of being directly administered, but it also can be dried and then packaged. The dried composition is mixed with sterilized aqueous solution immediately before administration to prepare a solution capable of being administered.

The composition according to the embodiment can be in a kit form. The kit of the embodiment comprises the aforementioned lipid particles and an introducer that introduces the lipid particles into cells, but the forms of them are not restricted. For example, the kit may comprise individual containers one of which holds a dispersion in which the lipid particles not combined with the activator is dispersed in a medium and another of which holds the activator; or otherwise the kit may comprise individual containers one of which holds the lipid particles in a dried form, another of which holds the activator and still another of which holds a medium. The lipid particles in a dispersion or in a dried form may be separated from the activator, and the lipid particles and the activator can be independently sold as individual products so that users can select the products according to their uses.

The kit can further comprise an agent used for introducing a nucleic acid.

[Way of Using Pharmaceutical Composition]

When the lipid particles of the embodiment is applied to medical uses, the composition can be employed for treatments or diagnoses of various human and animal diseases. Specifically, the lipid particles are combined with therapeutic agents as the activators so that the agents can be delivered to the target cells.

For example, various nucleic acids can be delivered to cells so that the cells may be brought into contact with the nucleic acids to prevent or treat diseases. Examples of the nucleic acids include: oligonucleotides, siRNAs, plasmids, antisenses, and ribozymes. The lipid compound of the embodiment can efficiently and smoothly catch and enclose those nucleic acids. Specifically, although it has hitherto been difficult to safely and rapidly introduce RNA into lipid particles, the lipid compound of the embodiment makes it possible and easy.

The lipid compound for preparing lipid particles and the compound for forming a membrane can be combined properly so as to realize effective cell targeting. For example, a set of the compounds (1-01) and (2-01), DOPE and cholesterol, a set of the compound (1-01) or (1-02), DOTAP and cholesterol, and a set of the compounds (1-01) and (2-01), DOTAP, DOPE and cholesterol are preferably employed for delivering to hepatoma cells, to T-cell leukemia cells, and to breast cancer cells, respectively.

Further, it becomes also possible by properly combining the lipid compound for preparing lipid particles with the compound for forming a membrane to realize effective diagnoses, treatments and prevention. For example, a set of the compounds (1-01) and (2-01), DOPE and cholesterol, a set of the compound (1-01) or (1-02), DOTAP and cholesterol, and a set of the compounds (1-01) and (2-01), DOTAP, DOPE and cholesterol are preferably employed for diagnosis, treatment and prevention of liver cancer, for diagnosis, treatment and prevention of T-cell leukemia, and for diagnosis, treatment and prevention of breast cancer, respectively.

The delivery of nucleic acids can be carried out either in vitro or in vivo. As the method of in-vivo dosing of the pharmaceutical composition, preferred is parenteral administration, such as, intraarticular administration, intravenous administration, intraperitoneal administration, subcutaneous administration, or intramuscular administration. The intravenous or intraperitoneal administration of the pharmaceutical composition can be carried out by bolus injection.

Further, the pharmaceutical composition of the embodiment can be directly spread and applied on the aimed tissues so as to bring the tissues into contact with the composition. The composition also can be administered to the meninges or the like by drip injection, and still also can be administered by endoscopy.

In a particular embodied case, the treatment with the pharmaceutical composition is generally carried out at a physiological temperature (about 37° C.) for 1 to 24 hours, preferably 2 to 8 hours. There are no particular restrictions on the target cells of in-vitro administration. For example, they may be cells of vertebrates, invertebrates or plants. However, preferred are animal cells, more preferred are mammal cells, and particularly preferred are human cells.

EXAMPLES

[Synthesis Example 1] Synthesis of the Compound (1-01)

According the aforementioned production process, the compound (1-01) was synthesized. Specific procedures thereof are described below.

First Step

Under an argon atmosphere, magnesium (17.38 g, 714.96 mol, 4.4 eq.), diethyl ether (165 mL) and iodine (7 mg) were placed in a 500-mL flask. After a few drops of 9-bromonon-1-ene (100.00 g, 487.47 mol, 3 eq.) were added at room temperature, the mixture was refluxed. While the mixture was kept refluxing, the rest of 9-bromonon-1-ene was dropped therein for 2 hours. After left overnight at room temperature, the Grignard reagent was poured into a dropping funnel while being washed with diethyl ether (40 mL). Into a 1000 mL four-neck flask in which ethyl formate (12.04 g, 162.49 mol, 1 eq.) and diethyl ether (165 mL) were beforehand placed, the Grignard reagent was dropped at a temperature of 0° C. or less for 1.5 hours.

After the reaction was let to proceed for 1 hour at room temperature, acetone (100 mL), water (200 mL) and 10% aqueous sulfuric acid (267 mL) were successively added and thereby the reaction mixture was separated. The aqueous layer was subjected to extraction with diethyl ether (300 mL), and the organic layer was dried with sodium sulfate. The crude product (72.1 g) obtained by filtration and concentration was purified by column chromatography (silica gel: 721 g, development: hexane to 3% ethyl acetate/97% hexane), to obtain the intermediate (1-01-1) as a while solid in an amount of 41.1 g (yield: 98%).

Second Step

Under an argon atmosphere, the intermediate (1-01-1) (41.1 g, 146.53 mmol, 1 eq.) was dissolved in dichloromethane (330 mL) and the solution was placed in a 1000 mL flask, to which triethylamine (59.31 g, 586.12 mmol, 4 eq.) and 4-dimethylaminopyridine (1.79 g, 14.65 mmol, 0.1 eq.) were then added. To the flask, methanesulfonyl chloride (33.57 g, 293.06 mmol, 2 eq.) was dropwise added at −5° C. After the mixture was stirred at room temperature for 1 hour, the reaction was quenched with ice water (17.6 mL). Successively, the reaction solution was washed with 1N hydrochloric acid (30 mL), water (300 mL) and saturated saline solution (300 mL), and then dried with sodium sulfate. The dried solution was filtrated and concentrated, to obtain the intermediate (1-01-2) as an orange oil in an amount of 49.6 g (yield: 94%).

Third Step

Under an argon atmosphere, DMF (300 mL) and sodium cyanide (13.56 g, 276.65 mmol, 2 eq.) were placed in a 1000-mL flask. After the intermediate (1-01-2) (49.6 g, 138.32 mmol, 1 eq.) dissolved in DMF (200 mL) was added, the mixture was heated at 55° C. and the reaction was let to proceed overnight. The reaction solution was then cooled to room temperature, diluted with water (500 mL), and three times repeatedly subjected to extraction with ethyl acetate (800 mL). The extracted organic layer was washed with water (500 mL) and saturated saline solution (500 mL), and then dried with sodium sulfate. The crude product (84.3 g) obtained by filtration and concentration was purified by column chromatography (silica gel: 1012 g, development: hexane to 5% ethyl acetate/95% hexane), to obtain the intermediate 3 as a pale yellow oil in an amount of 28.1 g (yield: 70%).

Fourth Step

Under an argon atmosphere, the intermediate (1-01-3) (28.1 g, 97.06 mmol, 1 eq.) and hexane (280 mL) were placed in a 2000-mL flask, to which 1M diisobutylaluminium hydride (DIBAL-H) dissolved in n-hexane (194.13 mL, 194.13 mmol, 2 eq.) was dropwise added at −70° C. After stirred at room temperature for 30 minutes, the mixture was cooled with ice to 0° C. and the reaction was quenched with methanol (14 mL). Subsequently, saturated aqueous ammonium chloride (1200 mL) was added to the reaction solution, which was then stirred for 20 minutes. Thereafter, 10% aqueous sulfuric acid (450 mL) was added and thereby the solution was separated. Successively, extraction was carried out twice with diethyl ether (500 mL). The extracted organic layer was washed with saturated aqueous sodium hydrogencarbonate (500 mL) and saturated saline solution (500 mL), and then dried with sodium sulfate. The solution was filtrated and concentrated, to obtain the intermediate (1-01-4) as a yellow oil in an amount of 25.3 g (yield: 89%).

Fifth Step

In a 1000 mL-flask, the intermediate (1-01-4) (25.3 g, 86.5 mmol, 1 eq.) and methanol (253 mL) were placed. After sodium borohydride (1.16 g, 30.27 mmol, 0.35 eq.) was added little by little at 0° C., the mixture was stirred overnight at room temperature. To the reaction solution, acetic acid (7 mL) was added until pH reached 4. After water (160 mL) was added, extraction was carried out three times with dichloromethane (400 mL) and then the organic layer was dried with sodium sulfate. The crude product (30.3 g) obtained by filtration and concentration was purified by column chromatography (silica gel: 304 g, development: 5% ethyl acetate/95% hexane), to obtain the intermediate (1-01-5) as a pale yellow oil in an amount of 22.13 g (yield: 87%).

Sixth Step

Under an argon atmosphere, the intermediate (1-01-5) (22.13 g, 75.14 mmol, 1 eq.) was dissolved in dichloromethane (220 mL) in a 1000-mL flask and then tetrabromomethane (29.90 g, 90.17 mmol, 1.2 eq.) was added therein. To the flask, triphenylphosphine (29.56 g, 112.71 mmol, 1.5 eq.) dissolved in dichloromethane (63 mL) was dropwise added at 0° C. After stirred at room temperature for 1 hour, the reaction solution was concentrated to obtain a crude product (21.3 g), which was then purified by column chromatography (silica gel: 200 g, development: hexane) to obtain the intermediate (1-01-6) as a colorless transparent oil in an amount of 14.5 g (yield: 54%).

Seventh Step

In a 1000 mL-flask, the intermediate (1-01-6) (5 g, 13.99 mmol, 1 eq.) was placed and dissolved in chloromethane (230 mL) and acetonitrile (230 mL). To the flask, ruthenium (III) chloride (145 mg, 0.69 mmol, Ru=40%) was added. Further, sodium periodate (29.92 g, 139.89 mmol, 10 eq.) dissolved in water (115 mL) was dropwise added at a temperature of 10° C. or less, and then the reaction solution was stirred overnight at room temperature. After the reaction was completed, water (230 mL) was added and thereby the solution was separated. The aqueous layer was subjected to extraction with dichloromethane (100 mL×twice), and thereafter saturated saline solution (230 mL) was added to the combined organic layer, to which 3% sodium sulfide was then added until the color changed. Subsequently, 1M hydrochloric acid was added until the solution became acidic and thereby the solution was separated. The organic layer was dried with sodium sulfate. The crude product (14.7 g) obtained by filtration and concentration was purified by column chromatography (silica gel: 300 g, development: chloroform to 2% methanol/98% chloroform), to obtain the intermediate (1-01-7) as a pale yellow oil in an amount of 2.73 g (yield: 49%).

Eighth Step

In a 100 mL-flask, the intermediate (1-01-7) (2.73 g, 6.94 mmol, 1 eq.) was dissolved in dichloromethane (45 mL). To the flask, cis-2-nonene-1-ol (2.41 g, 16.93 mmol, 2.44 eq), 4-dimethylaminopyridine (85 mg, 0.69 mmol, 0.1 eq.) and N,N-diisopropylethylamine (4.39 g, 34.01 mmol, 4.9 eq.) were added. Subsequently, 1-(3-dimethylamino-propyl)-3-ethylcarbodiimide hydrochloride (3.25 g, 16.93 mmol, 2.44 eq.) was added, and then the reaction solution was stirred overnight at room temperature. After the reaction was completed, the solution was diluted with dichloromethane (45 mL) and then washed successively with water (45 mL), 1M hydrochloric acid (90 mL), saturated aqueous sodium hydrogencarbonate (90 mL) and saturated saline solution (90 mL). The organic layer was dried with sodium sulfate. The crude product (3.7 g) obtained by filtration and concentration was purified by column chromatography (silica gel: 37 g, development: hexane to 5% ethyl acetate/95% hexane), to obtain the intermediate (1-01-8) as a pale yellow oil in an amount of 1.62 g (yield: 36%).

Ninth Step

In a 50-mL autoclave, the intermediate (1-01-8) (1.62 g, 2.52 mmol, 1 eq.) was dissolved in THF (30 mL). To the autoclave, N,N,N'-trimethylethylenediamine (5.16 g, 50.48 mmol, 20 eq.) and potassium carbonate (1.26 g, 9.09 mmol, 3.6 eq.) were added. The mixture was heated at 55° C. and let to react for 6 days. After the reaction was completed, the reaction solution was cooled to room temperature, diluted with dichloromethane (60 mL) and separated by adding water (30 mL). The aqueous layer was three times subjected to extraction with dichloro-methane (20 mL), and the combined organic layer was dried with sodium sulfate. The crude product (2.3 g) obtained by filtration and concentration was purified by column chromatography (silica gel: 25 g, development: chloroform to 5% methanol/95% chloroform), to obtain the aimed compound (1-01) as a pale yellow oil in an amount of 1.21 g (yield: 72%).

[Synthesis Example 2] Synthesis of the Compound (2-01)

According the aforementioned production process, the compound (2-01) was synthesized. Specific procedures thereof are described below.

Under an argon atmosphere, 5.00 g (33 mmol) of triethylene glycol, 14.39 mL (112 mmol) of triethylamine and acetonitrile (50 mL) were placed in a 200-mL flask, to which 7.97 mL (103 mmol) of methanesulfonyl chloride was then dropwise added at 0° C. Subsequently, the mixture was stirred for 1 hour at room temperature, and successively 10 mL of ethanol was dropwise added therein to treat unreacted methanesulfonyl chloride. After filtrated, the reaction solution was washed four times with 50 mL of dichloromethane and dried with $Na_2SO_4$. The dried reaction solution was filtrated and then concentrated to obtain the intermediate (2-01-1) as an orange oil in an amount of 8.21 g (yield: 81%).

Thereafter, 842 mg (2.75 mmol) of the intermediate (2-01-1), 950 mg (6.87 mmol) of $K_2CO_3$ and 15 mL of acetonitrile were placed in a 100-mL flask. After the mixture was stirred for 15 minutes at room temperature, 735 mg (8.258 mmol) of 3-(methylamino)-1-propanol was dropwise added. While the temperature was kept at 70° C., the mixture was stirred overnight. After the reaction solution was cooled, insolubles were removed by filtration. The filtrate was concentrated to obtain a crude product in an amount of 720 mg. The crude product was purified through a column chromatograph (15 g of NH silica-gel, developing solution: 50% hexane/chloroform), to obtain the intermediate (2-01-2) as a pale yellow transparent oil in an amount of 348 mg (yield: 43%).

In a 30-mL eggplant flask, 300 mg (1.03 mmol) of the intermediate (2-01-2) and 10 mL of dichloromethane were placed. After 770 mg (2.56 mmol) of retinoic acid, 50 mg (0.41 mmol) of 4-dimethylaminopyridine and 590 mg (3.08 mmol) of 1-(3-dimethyl-aminopropyl)-3-ethylcarbodiimide hydrochloride were added, the mixture was stirred at room temperature overnight. Subsequently, the reaction solution was washed twice with 10 mL of water, and then dried with $Na_2SO_4$. The dried solution was filtrated and concentrated to obtain a crude product in an amount of 2.1 g. The crude product was purified through a column chromatograph (40 g of silica-gel, developing solution: 50% hexane/chloroform and chloroform), to obtain the compound (2-01) as a deep orange oil in an amount of 262 mg (yield: 29%).

[Preparation of Lipid Compound-Containing Liposomes Enclosing DNA/Peptide Core Complex]

Solutions of vector DNA and a DNA condensing peptide were used to prepare a core complex comprising the vector DNA-DNA condensing peptide. The vector DNA employed here was a plasmid integrated with a cytomegalovirus early promoter/enhancer, a Nluc gene and a transcription terminator. The employed DNA condensing peptide was a mixture of mHP-1 (RQRQR-YY-RQRQR-GG-RRRRRR: sequence number 1) and mHP-2 (RRRRRR-YY-RQRQR-GG-RRRRRR: sequence number 2) in a ratio of 1:3.

The DNA condensing peptide solution (0.24 mg/ml, 10 mM HEPES, pH 7.3) in an amount of 100 µl was dispensed into a microtube (Proteosave SS [trademark]1.5 ml, manufactured by Sumitomo Bakelite Co., Limit.). While the dispensed peptide solution was being stirred with a vortex mixer (1500 rpm) (MSV-3500 [trademark], manufactured by Biosan Laboratories, Inc.), 200 µL of the vector DNA solution (0.15 mg/ml, 10 mM HEPES, pH 7.3) was dropwise added thereinto.

Liposomes enclosing the core complex were prepared according to an ethanol injection method. Into a microtube (Proteosave SS [trademark] 1.5 ml, manufactured by Sumitomo Bakelite Co., Limit.), 50 µl of the lipid solution having each blending ratio shown in Table 1 was dispensed. Here, as a comparative compound, the compound represented by the formula (R-1) was adopted.

TABLE 1

| | blending amounts (mole ratio) | | | | | | |
|---|---|---|---|---|---|---|---|
| | compound (1-01) | compound (2-01) | compound (R-01) | DOPE | DOTAP | cholesterol | DMG-PEG |
| Ex. 1-1 | 73 | 0 | 0 | 44 | 0 | 59 | 4 |
| Ex. 1-2 | 73 | 0 | 0 | 0 | 44 | 59 | 4 |
| Ex. 1-3 | 73 | 0 | 0 | 22 | 22 | 59 | 4 |
| Ex. 1-4 | 73 | 30 | 0 | 44 | 0 | 59 | 4 |
| Ex. 1-5 | 73 | 30 | 0 | 0 | 44 | 59 | 4 |
| Ex. 1-6 | 73 | 30 | 0 | 22 | 22 | 59 | 4 |
| Com. R-1 | 0 | 0 | 73 | 44 | 0 | 59 | 4 |
| Com. R-2 | 0 | 0 | 73 | 0 | 44 | 59 | 4 |

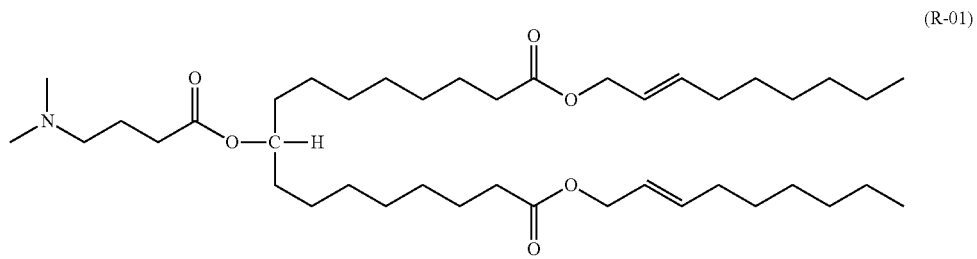 [SMILES: CCCCCC/C=C/COC(=O)CCCCCCCC(CCCCCCCC(=O)OC/C=C/CCCCCC)OC(=O)CCCN(C)C]

(R-01)

While the dispensed lipid solution was being stirred with a vortex mixer, 50 μl of the core complex was dropwise added thereinto. Thereafter, 400 μl of 10 mM HEPES (pH 7.3) was gently added to prepare liposomes enclosing the vector DNA. Further, 400 μl of 10 mM HEPES (pH 7.3) was added and gently mixed, and then the mixture was subjected to centrifugal buffer exchange and concentration by means of an ultrafiltration spin column (PT-1014 [trademark], manufactured by Apro Science Inc.), to prepare 100 μL of the core complex-enclosing liposomes (10 mM HEPES, pH 7.3).

[Evaluation of the Enclosed DNA Amount]

The amount of DNA enclosed in the obtained liposomes was measured by means of a Quant-iT PicoGreen dsDNA Assay Kit ([trademark], manufactured by Thermo Fisher Scientific Ltd.). The liposome solution in an amount of 5.0 μL was gently added to and suspended in 95 μL of a Tris-EDTA buffer solution containing 0.1% Triton-X100 [trademark], and the resultant suspended solution was left for 30 minutes at room temperature. Thereafter, the solution was mixed well with 100 μL of a PicoGreen solution diluted 200 times with the Tris-EDTA buffer solution. After the solution was left at room temperature for 5 minutes, the fluorescence intensity of the solution (excitation wavelength: 485 nm, emission wavelength: 530 nm) was measured with a microtiter plate reader (Mithras LB-940 [trademark], manufactured by Berthold Technologies GmbH & Co. KG). The DNA concentration was determined in reference to the standard curve produced with known concentrations of ADNA. From the obtained values, the amount of DNA enclosed in the liposomes was calculated as an amount per 1 mL of the solution (μg DNA/mL). The results are shown in Table 2.

It is thus revealed that the liposomes containing the compound of the formula (1-01) enclose DNA more than those containing the compound of the formula (R-01). Further, it is also verified that, if the compound of the formula (2) is adopted as the lipid compound in combination, the amount of enclosed DNA is increased.

[Measurement of Liposome Surface Charge]

The surface charge of liposomes (zeta potential) was measured with a Zetasizer (Zetasizer nonaZS [trademark], manufactured by Malvern Panalytical Ltd.). After 30 μL of the liposome solution was dispensed to a cell for zeta potential measurement (DTS-1070 [trademark], manufactured by Malvern Panalytical Ltd.), 870 μL of water was added therein and mixed. Subsequently, the cell was set in the Zetasizer to measure the zeta potential. The results are shown in Table 2.

From comparison of using only neutral lipid DOPE (Example 1-4) with using a combination of DOPE and cationic lipid DOTAP (Example 1-6) as the lipid forming a membrane, it was found that the latter can shift the zeta potential more to the plus side.

[Measurement of the Vector DNA Amount Introduced by Liposomes]

Figure 2:
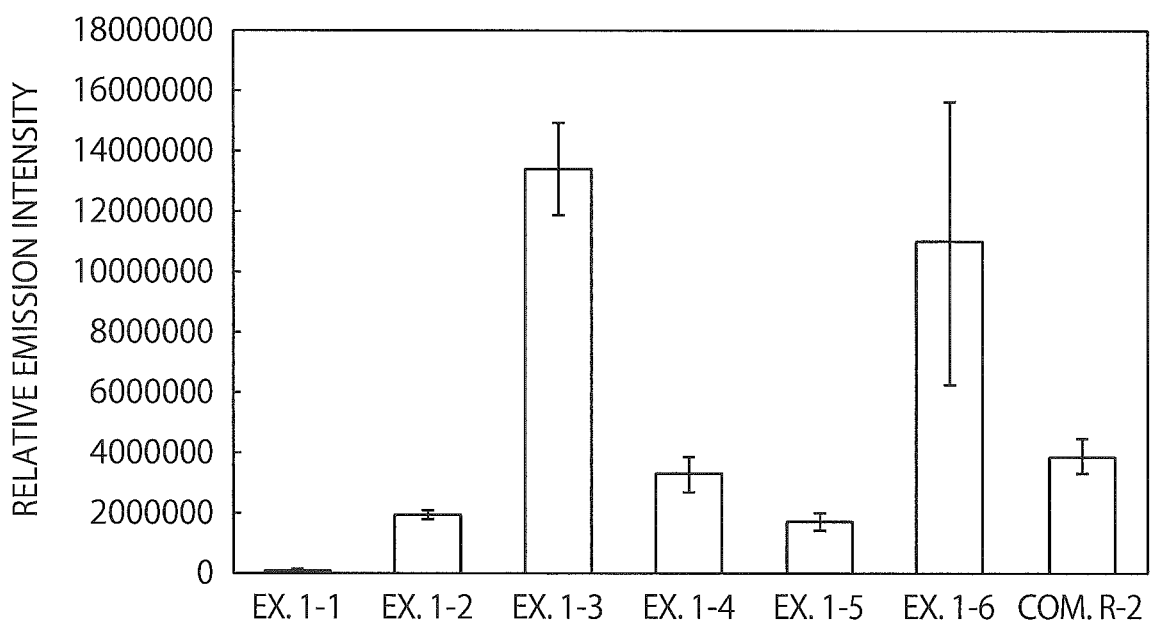
FIG. 2 is a graph showing enzyme activities when the lipid particles were applied to MCF-7 cells in examples and a comparative example.
Figure 3:
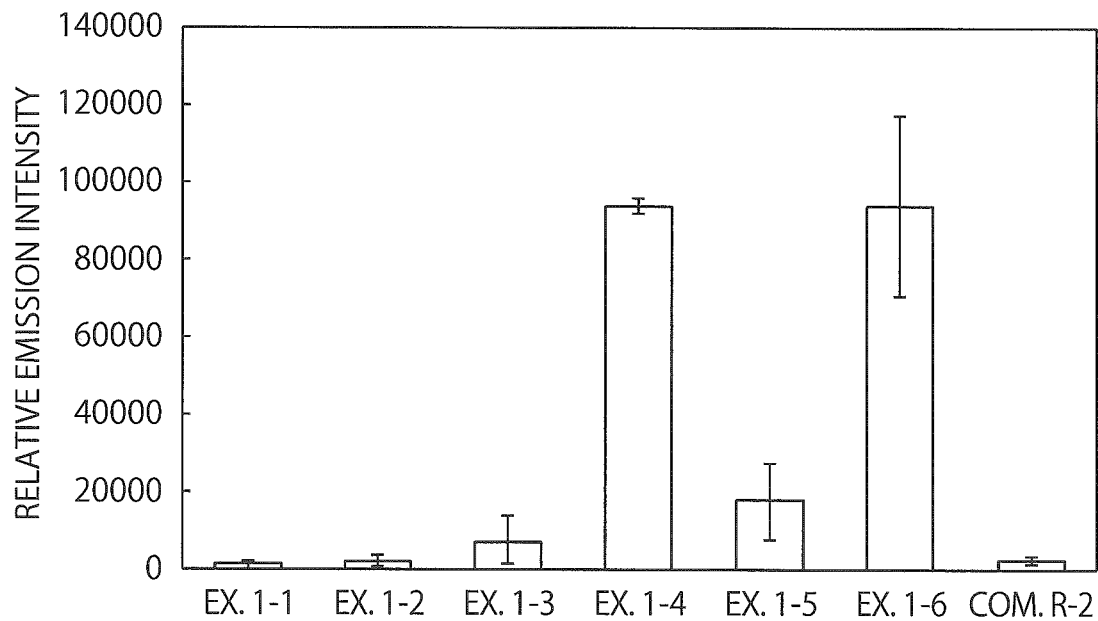
FIG. 3 is a graph showing enzyme activities when the lipid particles were applied to Huh-7 cells in examples and a comparative example.

The amount of vector DNA introduced to cells by the liposomes was quantified on the basis of expression of NLuc genes on vector DNA. For evaluating the expression of NLuc, emission thereof was measured with a microtiter plate reader (infinite F200 [trademark], manufactured by Tecan). As the cells, human T-cell leukemia cell lines Jurkat, human breast cancer cell lines MCF-7 or human liver cancer cell lines Huh-7 (purchased from American Type Culture Collection) were adopted. After 100 μL of the cell suspension ($1 \times 10^6$ cells/mL) was inoculated on a 96-well plate, 1 μL of each liposome solution shown in Table 1 was added. Thereafter, the cells were incubated in an incubator at 37° C. for 48 hours under an atmosphere of 5% $CO_2$, and then enzyme activity of NLuc was measured. The measurement of NLuc enzyme activity was carried out by use of NanoGlo Luciferase Assay System ([trademark], manufactured by Promega Corporation) with a luminometer according to the manual attached to the kit. The results are shown in FIG. 1 (Jurkat), FIG. 2 (MCF-7) and FIG. 3 (Huh-7).

It was thus verified that, if the lipid compound for forming a membrane is properly selected, the lipid compound of the formula (1) exhibits higher efficiency of NLuc gene expression than the comparative compound (R-01).

From the expression efficiency of NLuc gene introduced into cells by the liposomes, it is also revealed that the vector DNA is introduced more easily into adherent cells than into floating cells when the lipid compound of the formula (1) is combined with that of the formula (2). Further, it was still also revealed that preferences to cells different in proliferation type are dependent on surface charge controlled by whether DOTAP is contained or not.

TABLE 2

|         | amount of enclosed DNA | average zeta potential |
|---------|------------------------|------------------------|
| Ex. 1-1 | 15.7                   | 30.8                   |
| Ex. 1-2 | 19.9                   | 47.5                   |
| Ex. 1-3 | 19.8                   | 42.0                   |
| Ex. 1-4 | 21.2                   | 21.4                   |
| Ex. 1-5 | 25.5                   | 50.1                   |
| Ex. 1-6 | 23.9                   | 39.3                   |
| Com. R-1 | 2.0                   | 44.9                   |
| Com. R-2 | 17.5                  | 42.4                   |

[Synthesis Example 3] Synthesis of the Compound (1-02)

According the aforementioned production process, the compound (1-02) was synthesized. Specific procedures thereof are described below.

First Step

Under an argon atmosphere, magnesium (17.38 g, 714.96 mol, 4.4 eq.), diethyl ether (165 mL) and iodine (7 mg) were placed in a 500-mL flask. After a few drops of 9-bromonon-1-ene (100.00 g, 487.47 mol, 3.00 eq.) were added at room temperature, the mixture was refluxed. While the mixture was kept refluxing, the rest of 9-bromonon-1-ene was dropped therein for 2 hours. After left overnight at room temperature, the Grignard reagent was poured into a dropping funnel while being washed with diethyl ether (40 mL). Into a 1000 mL four-neck flask in which ethyl formate (12.04 g, 162.49 mol, 1.00 eq.) and diethyl ether (165 mL) were beforehand placed, the Grignard reagent was dropped at a temperature of 0° C. or less for 1.5 hours. After the reaction was let to proceed for 1 hour at room temperature, acetone (100 mL), water (200 mL) and 10% aqueous sulfuric acid (267 mL) were successively added and thereby the reaction mixture was separated. The aqueous layer was subjected to extraction with diethyl ether (300 mL), and the organic layer was dried with $Na_2SO_4$. The crude product (72.1 g) obtained by filtration and concentration was purified by column chromatography (silica gel: 721 g, development: hexane to 3% ethyl acetate/97% hexane), to obtain the intermediate (1-02-1) as a while solid in an amount of 41.1 g (yield: 98%).

Second Step

Under an argon atmosphere, the intermediate (1-02-1) (41.1 g, 146.53 mmol, 1.00 eq.) was dissolved in dichloromethane (330 mL) and the solution was placed in a 1000 mL flask, to which triethylamine (59.31 g, 586.12 mmol, 4.00 eq.) and 4-dimethylaminopyridine (1.79 g, 14.65 mmol, 0.10 eq.) were then added. To the flask, methanesulfonyl chloride (33.57 g, 293.06 mmol, 2.00 eq.) was dropwise added at −5° C. After the mixture was stirred at room temperature for 1 hour, the reaction was quenched with ice water (17.6 mL). Successively, the reaction solution was washed with 1N hydrochloric acid (30 mL), water (300 mL) and saturated saline solution (300 mL), and then dried with $Na_2SO_4$. The dried solution was filtrated and concentrated, to obtain the intermediate (1-02-2) as an orange oil in an amount of 49.6 g (yield: 94%).

Third Step

Under an argon atmosphere, DMF (300 mL) and sodium cyanide (13.56 g, 276.65 mmol, 2.00 eq.) were placed in a 1000-mL flask. After the intermediate (1-02-2) (49.6 g, 138.32 mmol, 1.00 eq.) dissolved in DMF (200 mL) was added, the mixture was heated at 55° C. and the reaction was let to proceed overnight. The reaction solution was then cooled to room temperature, diluted with water (500 mL), and subjected to extraction with ethyl acetate (800 mL×three times). The extracted organic layer was washed with water (500 mL) and saturated saline solution (500 mL), and then dried with $Na_2SO_4$. The crude product (84.3 g) obtained by filtration and concentration was purified by column chromatography (silica gel: 1012 g, development: hexane to 5% ethyl acetate/95% hexane), to obtain the intermediate (1-02-3) as a pale yellow oil in an amount of 28.1 g (yield: 70%).

Fourth Step

Under an argon atmosphere, the intermediate (1-02-3) (28.1 g, 97.06 mmol, 1.00 eq.) and hexane (280 mL) were placed in a 2000-mL flask, to which 1M DIBAL-n-hexane (194.13 mL, 194.13 mmol, 2.00 eq.) was dropwise added at −70° C. After stirred at room temperature for 30 minutes, the mixture was cooled with ice to 0° C. and the reaction was quenched with methanol (14 mL). Subsequently, saturated aqueous $NH_4Cl$ (1200 mL) was added to the reaction solution, which was then stirred for 20 minutes. Thereafter, 10% $H_2SO_4$ (450 mL) was added and thereby the solution was separated. Successively, extraction was carried out with diethyl ether (500 mL×twice). The extracted organic layer was washed with saturated aqueous $NaHCO_3$ (500 mL) and saturated saline solution (500 mL), and then dried with $Na_2SO_4$. The solution was filtrated and concentrated, to obtain the intermediate (1-02-4) as a yellow oil in an amount of 25.3 g (yield: 89%).

Fifth Step

In a 1000 mL-flask, the intermediate (1-02-4) (25.3 g, 86.5 mmol, 1.00 eq.) and methanol (253 mL) were placed. After sodium borohydride (1.16 g, 30.27 mmol, 0.35 eq.) was added little by little at 0° C., the mixture was stirred overnight at room temperature. To the reaction solution, acetic acid (7 mL) was added until pH reached 4. After water (160 mL) was added, extraction was carried out with dichloromethane (400 mL×three times) and then the organic layer was dried with $Na_2SO_4$. The crude product (30.3 g) obtained by filtration and concentration was purified by column chromatography (silica gel: 304 g, development: 5% ethyl acetate/95% hexane), to obtain the intermediate (1-02-5) as a pale yellow oil in an amount of 22.13 g (yield: 87%).

Sixth Step

Under an argon atmosphere, the intermediate (1-02-5) (22.13 g, 75.14 mmol, 1.00 eq.) was dissolved in dichloromethane (220 mL) in a 1000-mL flask and then tetrabromomethane (29.90 g, 90.17 mmol, 1.20 eq.) was added therein. To the flask, triphenylphosphine (29.56 g, 112.71 mmol, 1.50 eq.) dissolved in dichloromethane (63 mL) was dropwise added at 0° C. After stirred at room temperature for 1 hour, the reaction solution was concentrated to obtain a crude product (21.3 g), which was then purified by column chromatography (silica gel: 200 g, development: hexane) to obtain the intermediate (1-02-6) as a colorless transparent oil in an amount of 14.5 g (yield: 54%).

Seventh Step

Under an argon atmosphere, ethanol (90 mL) and 20% ethoxysodium (solvent: ethanol) (50.55 g, 148.57 mmol, 5.90 eq.) were placed in a 200 mL-flask and then heated at 65° C. Subsequently, diethyl malonate (24.20 g, 151.09 mmol, 6.00 eq.) and the intermediate (1-02-6) (9 g, 25.18 mmol, 1.00 eq.) were added and the mixture was heated to reflux overnight. After the reaction was completed, 1N hydrochloric acid (90 mL) was added for quenching at a temperature of 10° C. or less. The reaction mixture was then subjected to extraction with ethyl acetate (200 mL×three times), and the organic layer was washed successively with saturated aqueous $NaHCO_3$ (90 mL) and saturated saline solution (90 mL). The organic layer was dried with $Na_2SO_4$, filtrated and concentrated to obtain the intermediate (1-02-7) as an orange oil in an amount of 7.31 g (yield: 66%).

Eighth Step

In a 200 mL-flask, the intermediate (1-02-7) (7.31 g, 16.74 mmol, 1.00 eq.), dimethyl sulfoxide (70 mL) and sodium chloride (9.78 g, 167.40 mmol) were placed and the mixture was heated to reflux overnight. After the reaction was completed, the reaction solution was concentrated to obtain a crude product (21.3 g), which was then purified by column chromatography (silica gel: 200 g, development:

hexane to 2% ethyl acetate/98% hexane), to obtain the intermediate (1-02-8) as a pale yellow oil in an amount of 4.7 g (yield: 51%).

Ninth Step

Under an argon atmosphere, lithium aluminum hydride (734 mg, 19.34 mmol, 1.5 eq.) and THF (40 mL) were placed in a 200 mL four-neck flask, to which the intermediate (1-02-8) (4.7 g, 34.54 mmol, 1.00 eq.) dissolved in THF (40 mL) was then dropwise added at 0° C. and the reaction was let to proceed overnight at room temperature. Subsequently, the solution was cooled to 0° C. and the reaction was quenched with water (3.3 mL) and 15% sodium hydroxide (0.8 mL). After ethyl acetate (50 mL) was added, the reaction solution was filtrated through celite and the celite was washed with ethyl acetate (100 mL). The filtrate was concentrated to obtain a crude product (4.9 g), which was then purified by column chromatography (silica gel: 50 g, development: 5% ethyl acetate/95% hexane), to obtain the intermediate (1-02-9) as a colorless oil in an amount of 3.86 g (yield: 93%).

Tenth Step

Under an argon atmosphere, the intermediate (1-02-9) (3.86 g, 11.97 mmol, 1.00 eq.) was dissolved in dichloromethane (30 mL) and the solution was placed in a 1000 mL flask, to which triethylamine (4.87 g, 47.87 mmol, 4.00 eq.) and 4-dimethylaminopyridine (146 mg, 1.20 mmol, 0.10 eq.) were then added. To the flask, methanesulfonyl chloride (2.74 g, 23.93 mmol, 2.00 eq.) was dropwise added at −5° C. After the mixture was stirred at room temperature for 1 hour, the reaction was quenched with ice water (17.6 mL). Successively, the reaction solution was washed with 1N hydrochloric acid (10 mL), water (30 mL) and saturated saline solution (30 mL), and then dried with $Na_2SO_4$. The dried solution was filtrated and concentrated, to obtain the intermediate (1-02-10) as a brown oil in an amount of 4.79 g (yield: 99%).

Eleventh Step

Under an argon atmosphere, DMF (28 mL) and sodium cyanide (1.17 g, 23.94 mmol, 2.00 eq.) were placed in a 100-mL flask. After the intermediate (1-02-10) (4.79 g, 11.97 mmol, 1.00 eq.) dissolved in DMF (20 mL) was added, the mixture was heated at 55° C. and the reaction was let to proceed overnight. The reaction solution was then cooled to room temperature, diluted with water (50 mL), and subjected to extraction with ethyl acetate (100 mL×three times). The extracted organic layer was washed with water (50 mL) and saturated saline solution (50 mL), and then dried with $Na_2SO_4$. The crude product (11.4 g) obtained by filtration and concentration was purified by column chromatography (silica gel: 100 g, development: hexane to 5% ethyl acetate/95% hexane), to obtain the intermediate (1-02-11) as a colorless oil in an amount of 3.6 g (yield: 90%).

Twelfth Step

Under an argon atmosphere, the intermediate (1-02-11) (3.6 g, 10.86 mmol, 1.00 eq.) and hexane (36 mL) were placed in a 100-mL flask, to which 1M DIBAL-n-hexane (21.71 mL, 21.71 mmol, 2.00 eq.) was dropwise added at −70° C. After stirred at room temperature for 30 minutes, the mixture was cooled with ice to 0° C. and the reaction was quenched with methanol (1.6 mL). Subsequently, saturated aqueous $NH_4Cl$ (150 mL) was added to the reaction solution, which was then stirred for 20 minutes. Thereafter, 10% aqueous sulfuric acid (50 mL) was added and thereby the solution was separated. Successively, extraction was carried out with diethyl ether (50 mL×twice). The extracted organic layer was washed with saturated aqueous $NaHCO_3$ (50 mL) and saturated saline solution (50 mL), and then dried with $Na_2SO_4$. The solution was filtrated and concentrated, to obtain the intermediate (1-02-12) as a yellow oil in an amount of 3.2 g (yield: 88%).

Thirteenth Step

In a 100 mL-flask, the intermediate (1-02-12) (3.2 g, 9.56 mmol, 1.00 eq.) and methanol (32 mL) were placed. After sodium borohydride (127 mg, 3.35 mmol, 0.35 eq.) was added little by little at 0° C., the mixture was stirred overnight at room temperature. To the reaction solution, acetic acid (1 mL) was added until pH reached 4. After water (30 mL) was added, extraction was carried out with dichloromethane (30 mL×three times) and then the organic layer was dried with $Na_2SO_4$. The crude product (3.17 g) obtained by filtration and concentration was purified by column chromatography (silica gel: 32 g, development: 5% ethyl acetate/95% hexane), to obtain the intermediate (1-02-13) as a pale yellow oil in an amount of 1.12 g (yield: 35%).

Fourteenth Step

Under an argon atmosphere, the intermediate (1-02-13) (1 g, 2.97 mmol, 1.00 eq.) was dissolved in dichloromethane (10 mL) in a 30-mL flask and then tetrabromomethane (1.18 g, 3.57 mmol, 1.20 eq.) was added therein. To the flask, triphenylphosphine (1.17 g, 4.46 mmol, 1.50 eq.) dissolved in dichloromethane (5 mL) was dropwise added at 0° C. After stirred at room temperature for 1 hour, the reaction solution was filtrated and concentrated to obtain a crude product (7 g), which was then purified by column chromatography (silica gel: 70 g, development: hexane) to obtain the intermediate (1-02-14) as a colorless transparent oil in an amount of 1.12 g (yield: 94%).

Fifteenth Step

In a 200 mL-flask, the intermediate (1-02-14) (1.12 g, 2.80 mmol, 1.00 eq.) was placed and dissolved in dichloromethane (51 mL) and acetonitrile (51 mL). To the flask, ruthenium(III) chloride (29 mg, 0.14 mmol, Ru=40%) was added. Further, sodium periodate (5.99 g, 28.0 mmol, 10.00 eq.) dissolved in water (51 mL) was dropwise added at a temperature of 10° C. or less, and then the reaction solution was stirred overnight at a temperature of 10° C. or less. After the reaction was completed, water (51 mL) was added and thereby the solution was separated. To the organic layer, saturated saline solution (50 mL) was added and 3% aqueous $Na_2S$ was dropwise added until the color changed. Subsequently, 1N hydrochloric acid was added until the solution became acidic and thereby the solution was separated. The organic layer was dried with $Na_2SO_4$. The crude product (5.24 g) obtained by filtration and concentration was purified by column chromatography (silica gel: 50 g, development: chloroform to 5% methanol/95% chloroform), to obtain the intermediate (1-02-15) as a pale yellow oil in an amount of 1.05 g (yield: 86%).

Sixteenth Step

In a 100 mL-flask, the intermediate (1-02-15) (1.00 g, 2.30 mmol, 1.00 eq.) was dissolved in dichloromethane (30 mL). To the flask, cis-2-nonene-1-ol (797 mg, 5.60 mmol, 2.44 eq), 4-dimethylaminopyridine (28 mg, 0.23 mmol, 0.10 eq.) and N,N-diisopropylethylamine (1.45 g, 11.25 mmol, 4.90 eq.) were added. Subsequently, 1-(3-dimethyl-aminopropyl)-3-ethylcarbodiimide hydrochloride (1.07 g, 5.603 mmol, 2.44 eq.) was added, and then the reaction solution was stirred overnight at room temperature. After the reaction was completed, the solution was diluted with dichloromethane (30 mL) and then washed successively with water (30 mL), 1N hydrochloric acid (30 mL), saturated aqueous $NaHCO_3$ (30 mL) and saturated saline solution (30 mL). The organic layer was dried with $Na_2SO_4$. The crude product (1.92 g) obtained by filtration and concentration was purified by column chromatography (silica gel: 20 g, development: hexane to 2% ethyl acetate/98% hexane), to obtain the intermediate (1-02-16) as a pale yellow oil in an amount of 77 mg (yield: 5%).

Seventeenth Step

In a 50-mL autoclave, the intermediate (1-02-16) (77 mg, 0.11 mmol, 1.00 eq.) was dissolved in THF (3 mL). To the autoclave, 1-methylpiperazine (225 mg, 2.25 mmol, 20.00 eq.) and potassium carbonate (56 mg, 0.41 mmol, 3.6 eq.) were added. The mixture was heated at 55° C. and let to react for 6 days. After the reaction was completed, the reaction solution was cooled to room temperature, diluted with dichloromethane (6 mL) and separated by adding water (5 mL). The aqueous layer was subjected to extraction with dichloromethane (6 mL×three times), and the combined organic layer was dried with $Na_2SO_4$. The crude product (108 mg) obtained by filtration and concentration was purified by column chromatography (silica gel: 1 g, development: chloroform to 10% methanol/90% chloroform), to obtain the compound (1-02) as a thick yellow oil in an amount of 54 mg (yield: 68%).

[Preparation of Lipid Compound-Containing Liposomes Enclosing DNA/Peptide Core Complex]

Solutions of vector DNA and a DNA condensing peptide were used to prepare a core complex comprising the vector DNA-DNA condensing peptide. The vector DNA employed here was a plasmid integrated with a cytomegalovirus early promoter/enhancer, a Nluc gene and a transcription terminator. The employed DNA condensing peptide was a mixture of mHP-1 (RQRQR-YY-RQRQR-GG-RRRRRR: sequence number 1) and mHP-2 (RRRRRR-YY-RQRQR-GG-RRRRRR: sequence number 2) in a ratio of 4:1.

The DNA condensing peptide solution (0.255 mg/ml, 10 mM HEPES, pH 7.3) in an amount of 100 μl was dispensed into a microtube (Proteosave SS [trademark] 1.5 ml, manufactured by Sumitomo Bakelite Co., Limit.). While the dispensed peptide solution was being stirred with a vortex mixer (1500 rpm) (MSV-3500 [trademark], manufactured by Biosan Laboratories, Inc.), 200 μL of the vector DNA solution (0.15 mg/ml, 10 mM HEPES, pH 7.3) was dropwise added thereinto.

Liposomes enclosing the core complex were prepared according to an ethanol injection method. Into a microtube (Proteosave SS [trademark] 1.5 ml, manufactured by Sumitomo Bakelite Co., Limit.), 50 μl of the lipid solution having each blending ratio shown in Table 3 was dispensed. Reference examples 2-1 and 2-2 in Table 3 were prepared newly by the same procedures as Examples 1-2 and 1-4 described above, respectively.

While the dispensed lipid solution was being stirred with a vortex mixer, 50 μl of the core complex was dropwise added thereinto. Thereafter, 900 μl of 10 mM HEPES (pH 7.3) was gently added to prepare liposomes enclosing the vector DNA. The solution was subjected to centrifugal buffer exchange and concentration by means of an ultrafiltration filter (Centriprep YM-50 [trademark], manufactured by Merck KGaA). As a result, 32 ml of the core complex-enclosing liposomes was concentrated to 600 μL.

[Evaluation of the Enclosed DNA Amount]

The amount of DNA enclosed in the obtained liposomes was measured by means of a Quant-iT PicoGreen dsDNA Assay Kit ([trademark], manufactured by Thermo Fisher Scientific Ltd.). The liposome solution in an amount of 0.5 μL was gently added to and suspended in 99.5 μL of a Tris-EDTA buffer solution containing 0.1% Triton-X100 [trademark] and heparin sodium salt (Sigma-Aldrich Japan), and the resultant suspended solution was left for 30 minutes at room temperature. Thereafter, the solution was mixed well with 100 μL of a PicoGreen solution diluted 200 times with the Tris-EDTA buffer solution. After the solution was left at room temperature for 5 minutes, the fluorescence intensity of the solution (excitation wavelength: 485 nm, emission wavelength: 530 nm) was measured with a microtiter plate reader (Mithras LB-940 [trademark], manufactured by Berthold Technologies GmbH & Co. KG).

The DNA concentration was determined in reference to the standard curve produced with known concentrations of λDNA. From the obtained values, the amount of DNA enclosed in the liposomes was calculated as an amount per 1 mL of the solution (μg DNA/mL). The results are shown in Table 4.

It is thus revealed that the liposomes containing the compound of the formula (1-02) enclose DNA similarly to those containing the compound of the formula (1-01). Further, it is also verified that, if the compound of the formula (2-01) is used in combination, the amount of enclosed DNA is increased.

[Measurement of Liposome Surface Charge]

The surface charge of liposomes (zeta potential) was measured with a Zetasizer (Zetasizer nonaZS [trademark], manufactured by Malvern Panalytical Ltd.). After 10 μL of the liposome solution was dispensed to a cell for zeta potential measurement (DTS-1070 [trademark], manufactured by Malvern Panalytical Ltd.), 890 μL of distilled water was added therein and mixed. Subsequently, the cell was set in the Zetasizer to measure the zeta potential. The results are shown in Table 4.

From comparison of using neutral lipid DOPE Reference example 2-2 and Example 2-2) with using not DOPE but cationic lipid DOTAP (Reference example 2-1 and Example 2-1) as the lipid forming a membrane, it was found that the latter can shift the zeta potential more to the plus side.

TABLE 3

| | blending amounts (mole ratio) | | | | | | |
|---|---|---|---|---|---|---|---|
| | compound (1-01) | compound (1-02) | compound (2-01) | DOPE | DOTAP | cholesterol | DMG-PEG |
| Ref. 2-1 | 73 | 0 | 0 | 0 | 44 | 59 | 4 |
| Ref. 1-2 | 73 | 0 | 30 | 44 | 0 | 59 | 4 |
| Ex. 2-1 | 0 | 73 | 0 | 0 | 44 | 59 | 4 |
| Ex. 2-2 | 0 | 73 | 30 | 44 | 0 | 59 | 4 |

[Measurement of the Vector DNA Amount Introduced by Liposomes]

Figure 4:
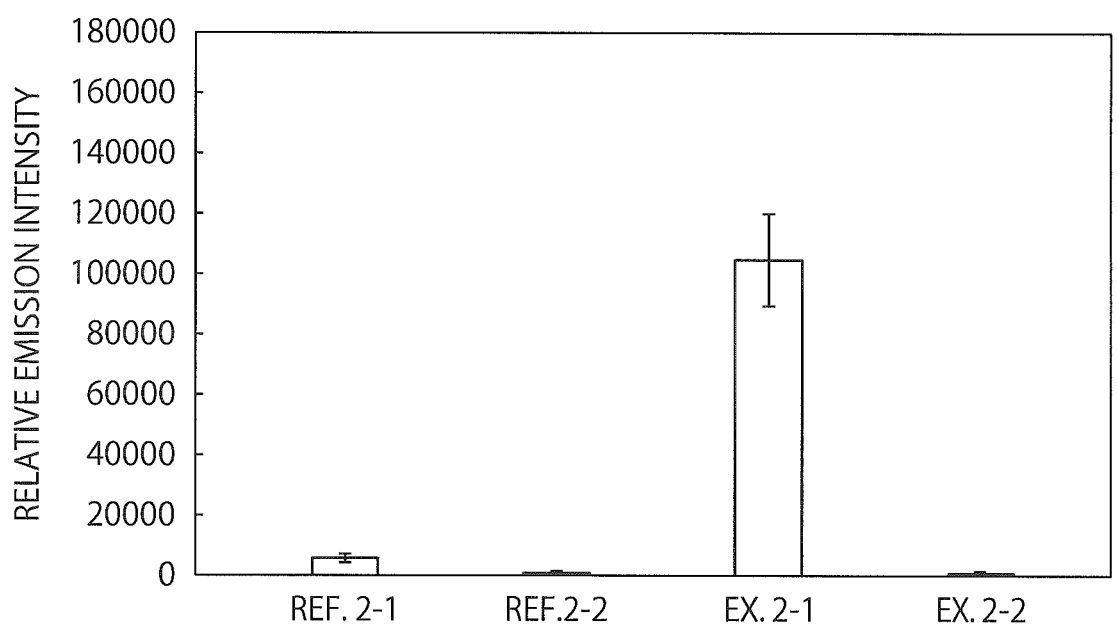
FIG. 4 is a graph showing enzyme activities when the lipid particles were applied to Jurkat cells in examples.
Figure 5:
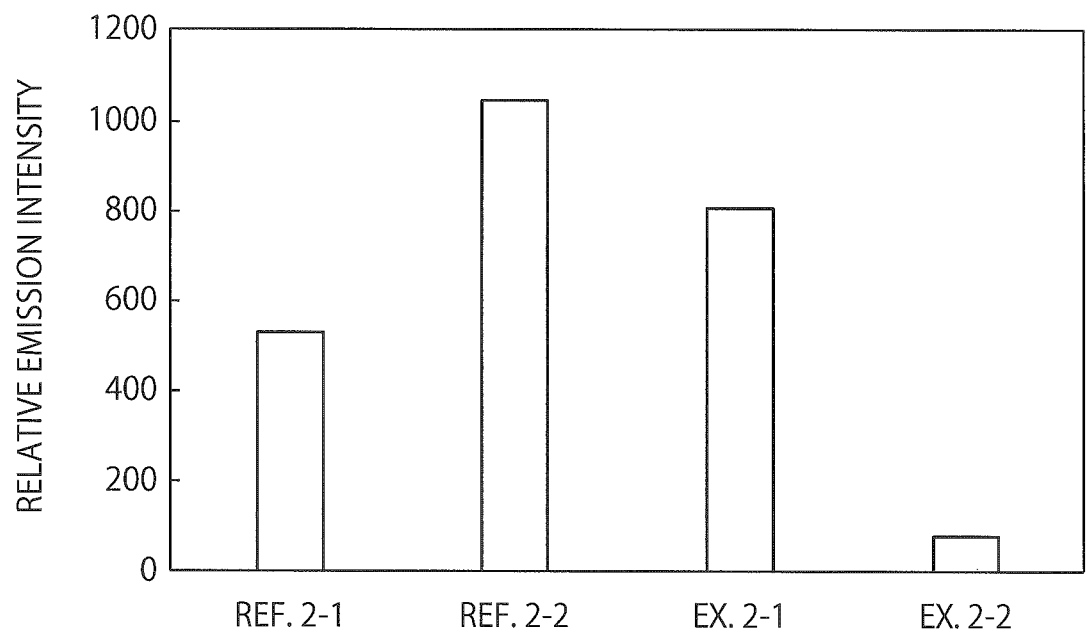
FIG. 5 is a graph showing enzyme activities when the lipid particles were applied to peripheral blood mononuclear cells (PBMCs) in examples.

The amount of vector DNA introduced to cells by the liposomes was quantified on the basis of expression of NLuc genes on vector DNA. For evaluating the expression of NLuc, emission thereof was measured with a microtiter plate reader (infinite F200 [trademark], manufactured by Tecan). As the cells, human T-cell leukemia cell lines Jurkat (purchased from American Type Culture Collection) and human peripheral blood mononuclear cells PBMCs (purchased from LONZA Japan) were adopted. After 100 μL of the Jurkat cell suspension ($1 \times 10^6$ cells/mL) and 100 μL of the PBMC cell suspension ($5 \times 10^6$ cells/mL) were individually inoculated on a 96-well plate, 1 μL of each liposome solution shown in Table 1 was added so that the DNA amount might be 0.8 μg/well. Thereafter, the cells were incubated in an incubator at 37° C. for 48 hours under an atmosphere of 5% $CO_2$, and then enzyme activity of NLuc was measured. The measurement of NLuc enzyme activity was carried out by use of NanoGlo Luciferase Assay System ([trademark], manufactured by Promega Corporation) with a luminometer according to the manual attached to the kit. The results are shown in FIG. 4 (Jurkat) and FIG. 5 (PBMC).

It was thus verified that, if DOTAP is selected as the lipid compound for forming a membrane, the lipid compound of the formula (1-02) exhibits higher efficiency of NLuc gene expression in Jurkat cells than the compound of the formula (1-01). Further, it is also verified that, if a set of the compound (2-01) and DOPE is selected as the lipid compound for forming a membrane, the lipid compound of the formula (1-01) exhibits higher efficiency of NLuc gene expression in PBMC cells than the compound of the formula (1-02).

TABLE 4

|  | amount of enclosed DNA | average zeta potential |
| --- | --- | --- |
| Ref. 2-1 | 183.9 | 51.5 |
| Ref. 2-2 | 162.5 | 34.4 |
| Ex. 2-1 | 188 | 52.6 |
| Ex. 2-2 | 131.4 | 43.9 |

[Lipid Compound-Containing Liposomes Enclosing RNA]
[Preparation of Liposomes Enclosing RNA]

The adopted messenger RNA (mRNA) was a green fluorescent protein (GFP) mRNA (OZ Biosciences), which functions as a reporter gene. The RNA-enclosing liposomes were prepared by the steps of: adding a GFP mRNA solution to a lipid solution having each blending ratio shown in Table 5; suspending the mixture by pipetting; gently adding 10 mM HEPES (pH 7.3); and washing and concentrating the solution by centrifugal ultrafiltration. Here, as a comparative compound, the compound represented by the formula (R-1) was adopted. Comparative example R-3 was prepared newly by the same procedures as Comparative example R-1.

TABLE 5

| | blending amounts (mole ratio) | | | | | | |
| --- | --- | --- | --- | --- | --- | --- | --- |
| | compound (1-01) | compound (1-02) | compound (R-01) | DOPE | DOTAP | cholesterol | DMG-PEG |
| Ex. 3-1 | 73 | 0 | 0 | 44 | 0 | 59 | 4 |
| Ex. 3-2 | 0 | 73 | 0 | 44 | 0 | 59 | 4 |
| Com. R-3 | 0 | 0 | 73 | 44 | 0 | 59 | 4 |

[Measurement of the Enclosed RNA Amount]

The amount of RNA enclosed in the liposomes was measured by means of a Quant-iT PicoGreen dsDNA Assay Kit ([trademark], manufactured by Thermo Fisher Scientific Ltd.). The measurement was carried out according to the manual attached to the kit. The results are shown in Table 6.

As a result, it was found that there was no particular difference in the amount of enclosed RNA among the RNA-enclosed liposomes prepared from the lipid solutions having the blending ratios shown in Table 5.

TABLE 6

|  | amount of enclosed RNA | average zeta potential |
| --- | --- | --- |
| Ex. 3-1 | 142.3 | 27.5 |
| Ex. 3-2 | 135.8 | 42.5 |
| Com. R-3 | 144.0 | 39.8 |

[Measurement of Liposome Surface Charge]

The surface charge of liposomes (zeta potential) was measured with a Zetasizer (Zetasizer nonaZS [trademark], manufactured by Malvern Panalytical Ltd.). The liposome solution was poured into a cell for zeta potential measurement (DTS-1070 [trademark], manufactured by Malvern Panalytical Ltd.), and then diluted and mixed with distilled water. Subsequently, the cell was set at the predetermined position in the Zetasizer to measure the zeta potential. As a result, the RNA-enclosing liposomes prepared according to Table 5 were found to enclose RNA in amounts shown in Table 6 and to have the zeta potentials shown in Table 6.

[Measurement of the RNA Amount Introduced by Liposomes]

Figure 6:
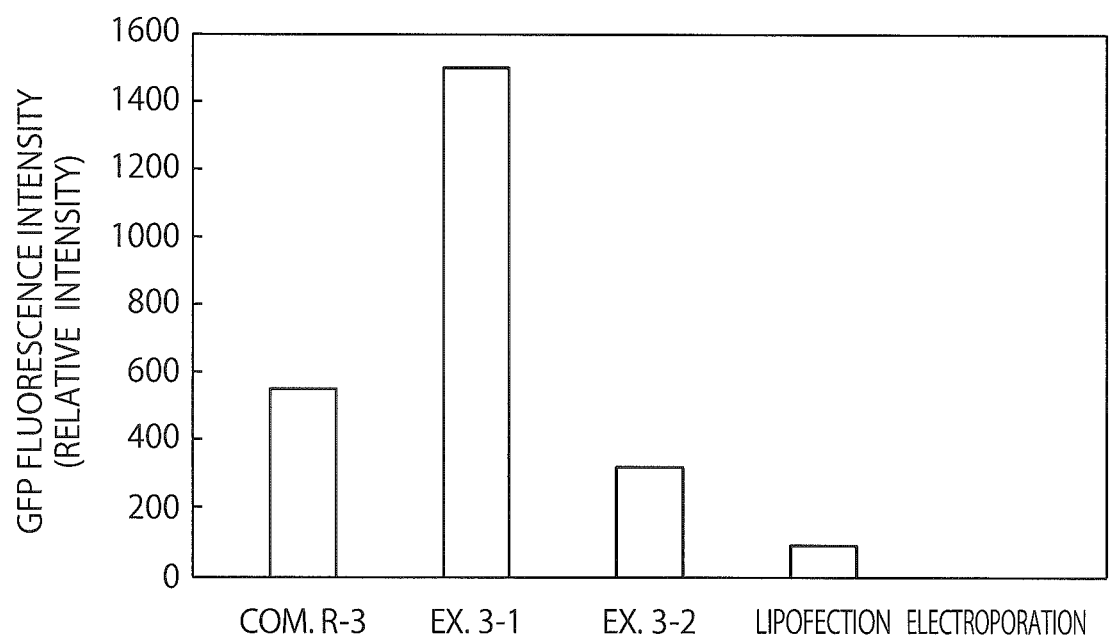
FIG. 6 is a graph showing RNA expression levels when the lipid particles were used to introduce RNA molecules into Jurkat cells in examples and a comparative example.

The amount of RNA introduced to cells by the liposomes was quantified on the basis of expression of GFP genes encoded by RNA. For evaluating the expression of GFP genes, emission thereof was measured with a flow cytometer (FACSVerse [trademark], manufactured by BD Biosciences Ltd.). As the cells, human T-cell leukemia cell lines Jurkat (purchased from American Type Culture Collection) were adopted. After incubated in TexMACS medium (manufactured by Gibco), the Jurkat cells were recovered by centrifugation and then so suspended in fresh TexMACS that the concentration might be $0.65 \times 10^7$ cells/mL. The cell suspension and TexMACS in amounts of 150 μl each were dispensed to a 48-well incubation plate so that the cell amount might be $1.0 \times 10^6$ cells/well. Thereafter, the RNA-enclosing liposomes shown in Table 5 were so added to the wells that the GFP RNA amount might be 0.5 μg/well, and then the mixtures were incubated at 37° C. under an atmosphere of 5% $CO_2$. Independently, as comparative RNA-introduction methods, lipofection with a Lipofectamine reagent (Lipofectamine 3000 [trademark], manufactured by Invitrogen) and electroporation were carried out to introduce RNA. The introduction by lipofection was carried out according to the manual attached to the reagent. On the other hand, the introduction by electroporation was carried out in the following manner. After the Jurkat cells were recovered by centrifugation, OptiMEM (GiBco) was added to wash the cells. The cells were then recovered again by centrifugation, and then so suspended in OptiMEM that the concentration might be $1.0 \times 10^7$ cells/mL. To 100 μL of the cell suspension, 0.5 μg of GFP RNA was added. The mixture was transferred to a cuvette electrode, and then electroporation was carried out by means of CUY21 EDIT II (BEX) under the following conditions.
<Poring Pulse (Pp) Conditions>
Pp, 225 V; Pp on, 2.5 ms; Pp off, 50.0 ms
<Driving Pulse (Pd) Conditions>
Pd, 20 V; Pd on, 50.0 ms; Pd off, 50.0 ms; 5 cycle; Capacitor, 1416.3 μF After incubated for 48 hours, the cells to which GFP RNA was introduced were recovered and suspended in a phosphate buffer solution PBS containing 1% BSA (Gibco). Subsequently, GFP fluorescence intensity (green fluorescence intensity) emitted from the cells was measured with a flow cytometer. FIG. 6 is a graph showing the measurement results. In the graph, relative fluorescence intensity was plotted on the vertical axis. As a result, it was revealed that the RNA-enclosing liposomes prepared from the lipid solutions of Examples 3-1 and 3-2 exhibit higher introduced amounts than those obtained by other RNA-introduction methods, such as, lipofection and electroporation. Further, it was also found that, among the RNA-enclosing liposomes, the liposomes containing the lipid solution of Example 3-1 shows the highest introduced amount.

[Measurement of the Vector DNA Amount Introduced by Liposomes]

In the same manner as Examples 1-3, 1-4 and 1-6, liposomes enclosing a core complex which contains plasmid expressing NLuc were prepared (Examples 4-1, 4-2 and 4-3). Table 7 shows the lipid solution compositions of those liposomes and the results of surface charge measurement.

TABLE 7

|  | blending amounts (mole ratio) | | | | | | average zeta potential (mV) |
| --- | --- | --- | --- | --- | --- | --- | --- |
|  | compound (1-01) | compound (2-01) | DOPE | DOTAP | cholesterol | DMG-PEG |  |
| Ex. 4-1 | 73 | 0 | 22 | 22 | 59 | 4 | 42.0 |
| Ex. 4-2 | 73 | 30 | 22 | 22 | 59 | 4 | 39.3 |
| Ex. 4-3 | 73 | 30 | 44 | 0 | 59 | 4 | 21.4 |

The amount of vector DNA introduced to cells by the liposomes was quantified on the basis of expression of NLuc genes on vector DNA. For evaluating the expression of NLuc, emission thereof was measured with a microtiter plate reader (infinite F200 [trademark], manufactured by Tecan). As the cells, human T-cell leukemia cell lines Jurkat, human breast cancer cell lines MCF-7 and human liver cancer cell lines Huh-7 (purchased from American Type Culture Collection) were adopted. After 100 μL of the cell suspension ($1 \times 10^6$ cells/mL) was inoculated on a 96-well plate, 1 μL of each liposome solution shown in Table 7 was added. Thereafter, the cells were incubated in an incubator at 37° C. for 48 hours under an atmosphere of 5% $CO_2$, and then enzyme activity of NLuc was measured. The measurement of NLuc enzyme activity was carried out by use of NanoGlo Luciferase Assay System ([trademark], manufactured by Promega Corporation) with a luminometer according to the manual attached to the kit. The results are shown in FIGS. 7 to 11.

Figure 7:
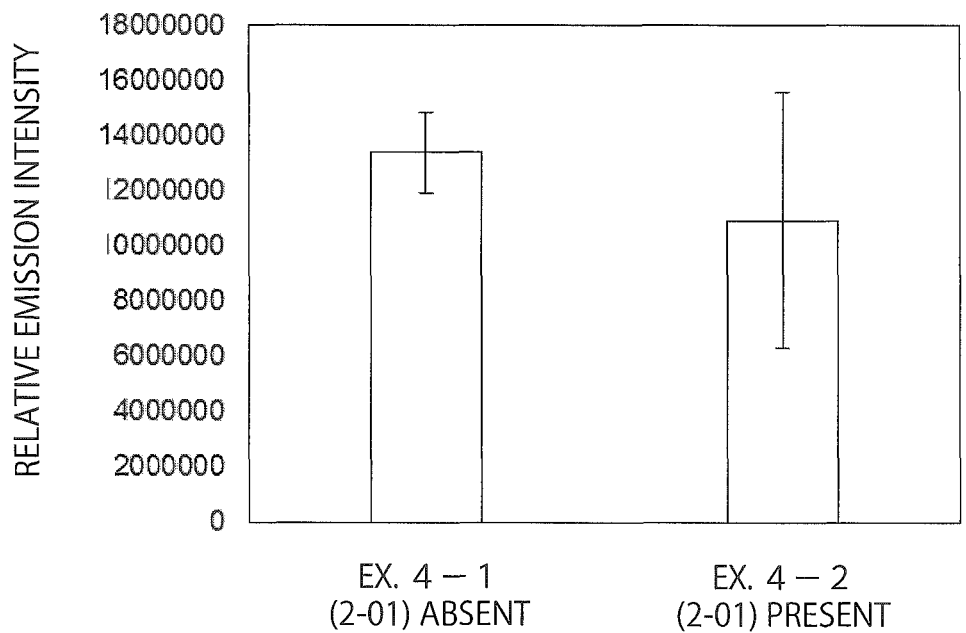
FIG. 7 is a graph showing enzyme activities when the lipid particles were applied to MCF-7 cells for the purpose of comparison between Examples 4-1 and 4-2.
Figure 8:
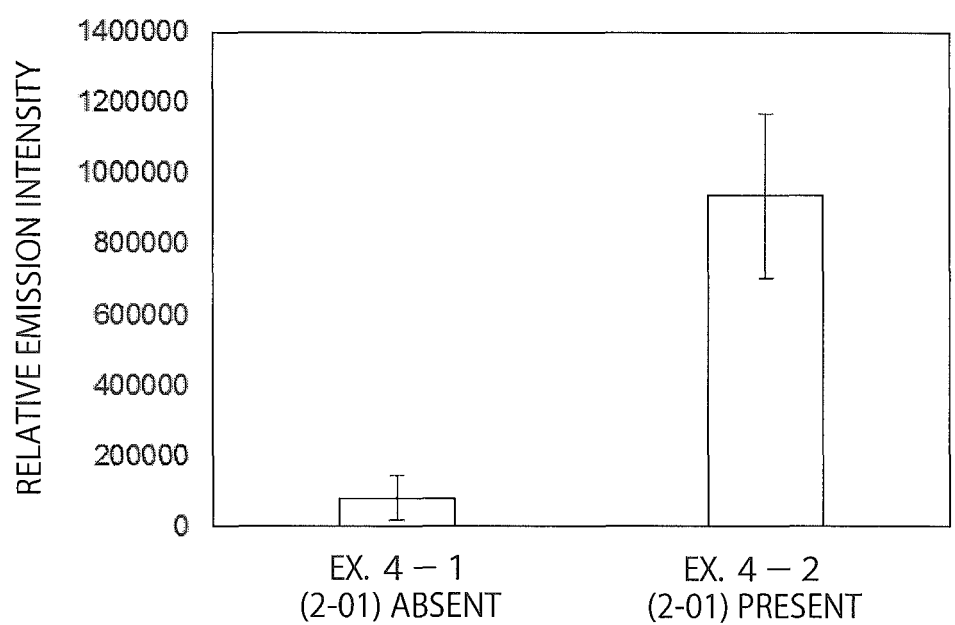
FIG. 8 is a graph showing enzyme activities when the lipid particles were applied to Huh-7 cells for the purpose of comparison between Examples 4-1 and 4-2.
Figure 9:
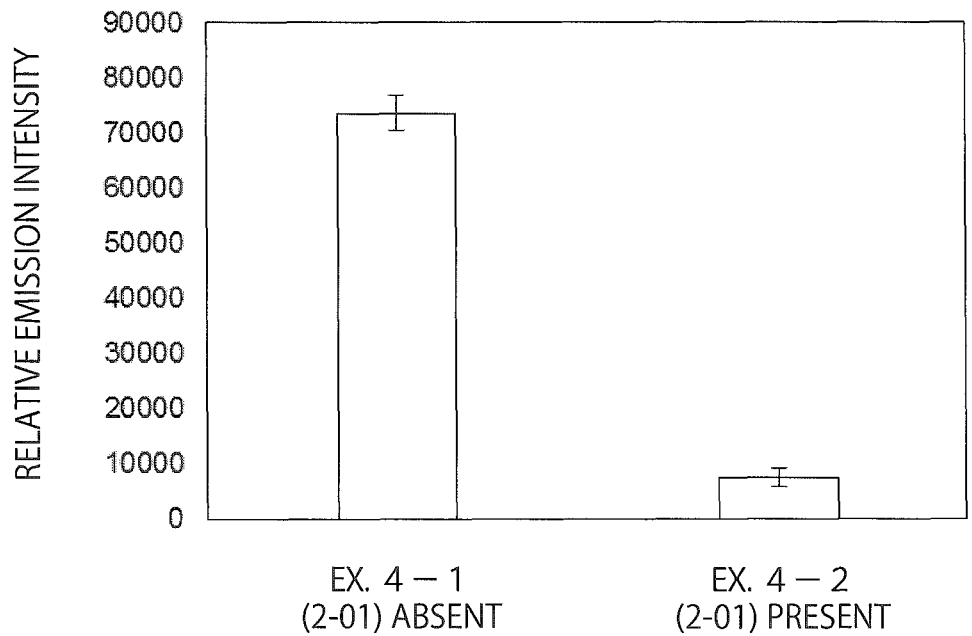
FIG. 9 is a graph showing enzyme activities when the lipid particles were applied to Jurkat cells for the purpose of comparison between Examples 4-1 and 4-2.

FIGS. 7 to 9 show graphs in which Examples 4-1 and 4-2 are compared. Specifically, FIGS. 7, 8 and 9 exhibit expression efficiencies of NLuc genes in breast cancer cells (cell lines MCF-7), in liver cancer cells (cell lines Huh-7) and in leukemia cells (T-lymphocytes, cell lines Jurkat), respectively. The results shown in FIGS. 7 to 9 indicate that incorporation of the compound (2-01) makes the vector DNA enclosed in liposomes more easily introduced into adherent cells than into floating cells.

Figure 10:
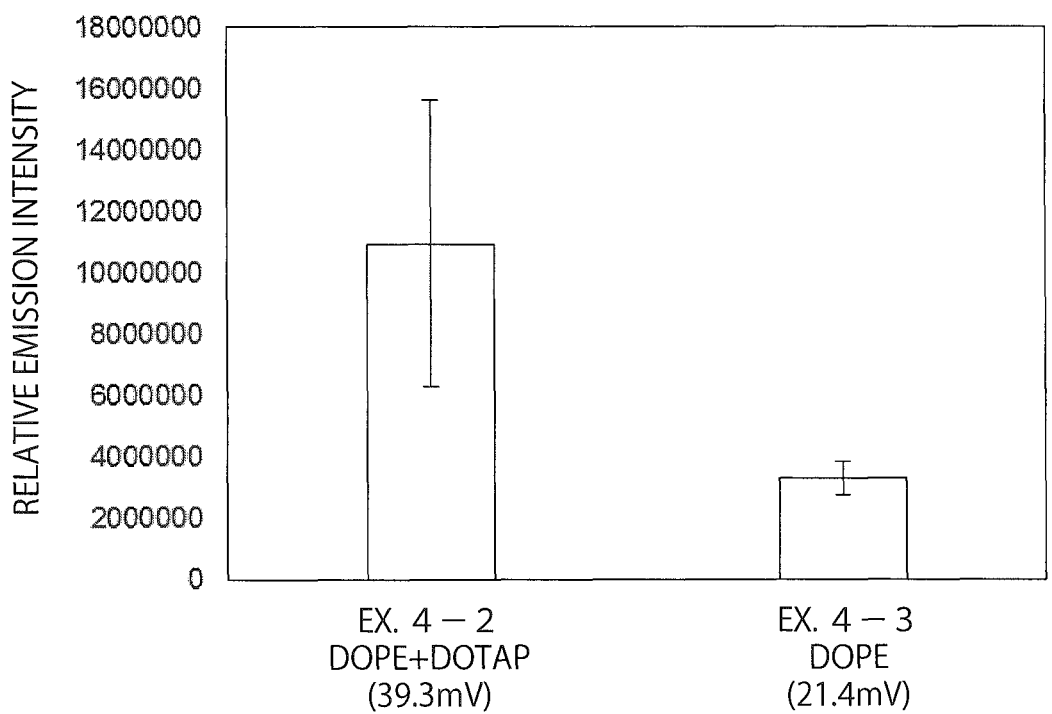
FIG. 10 is a graph showing enzyme activities when the lipid particles were applied to MCF-7 cells for the purpose of comparison between Examples 4-2 and 4-3.
Figure 11:
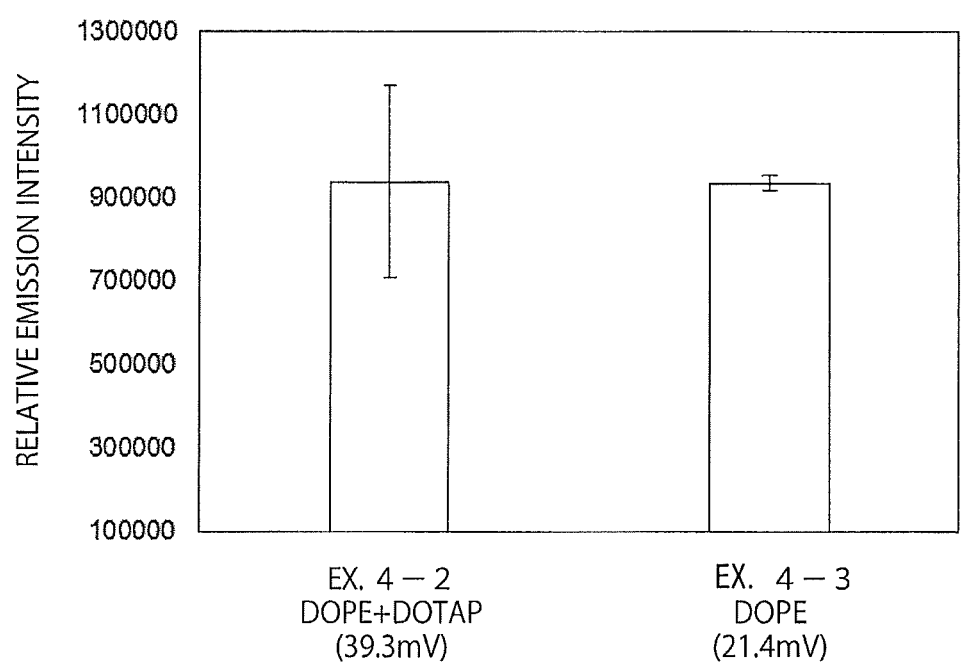
FIG. 11 is a graph showing enzyme activities when the lipid particles were applied to Huh-7 cells for the purpose of comparison between Examples 4-2 and 4-3.

FIGS. 10 and 11 show graphs in which Examples 4-2 and 4-3 are compared. Specifically, FIGS. 10 and 11 exhibit expression efficiencies of NLuc genes in breast cancer cells (cell lines MCF-7) and in liver cancer cells (cell lines Huh-7), respectively. From the results shown in FIGS. 10 to 11, it was found that the liposomes containing a set of the compounds (1-01) and (2-01) can be made to have preferences to cells different in proliferation type by whether or not DOTAP is used to control the surface charge thereof.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fail within the scope and sprit of the invention.

The invention claimed is:

1. A compound represented by the formula (1):

$$Q\text{-}CHR_2 \tag{1}$$

wherein

Q is a nitrogen-containing aliphatic group containing two or more tertiary nitrogens but no oxygen, and each R is independently an aliphatic group of $C_{12}$ to $C_{24}$, and is represented by the following formula (1-R):

$$-L^{R1}\text{-}C(=O)\text{-}O\text{-}L^{R2} \tag{1-R}$$

wherein $L^{R1}$ is alkylene, and $L^{R2}$ is represented by the following formula (1-R2);

$$-CH_2\text{-}CH=CH\text{-}(CH_2)_{r2}\text{-}H \tag{1-R2}$$

wherein r2 is an integer of 1 to 10.

2. The compound according to claim 1, wherein said Q is represented by the following formula (1-Q):

$$R^{Q1}{}_2N\text{—}(CR^{Q2}{}_2)_{q1}\text{—}NR^{Q1}\text{—}(CR^{Q2}{}_2)_{q2}\text{—}* \tag{1-Q}$$

wherein each $R^{Q1}$ is independently an alkyl, each $R^{Q2}$ is independently hydrogen or an alkyl, any two of $R^{Q1}$s and $R^{Q2}$s may link together to form a nitrogen-containing alicyclic ring, q1 is an integer of 1 to 4, q2 is an integer of 0 to 4, and the mark * indicates the position bonding to —$CHR_2$.

3. The compound according to claim 1, wherein said Q has any of the following structures:

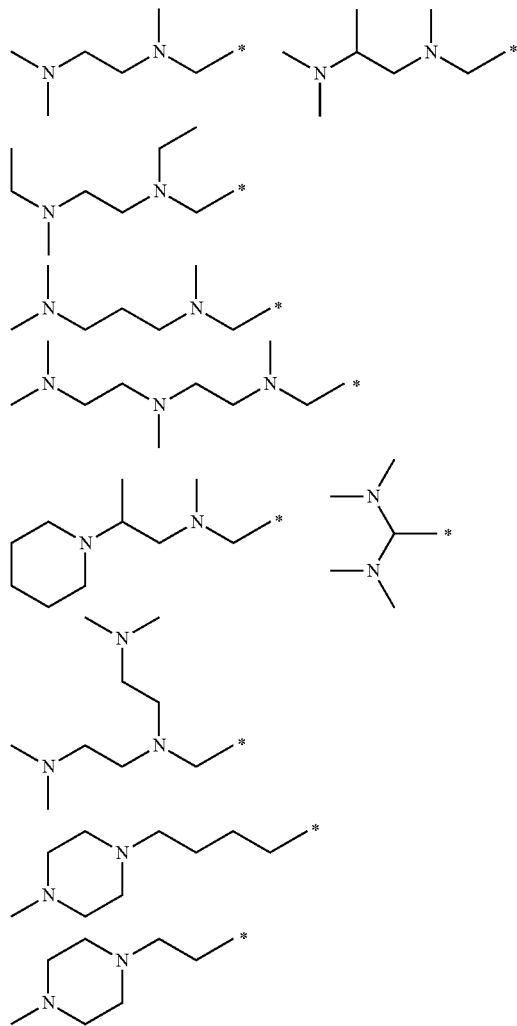
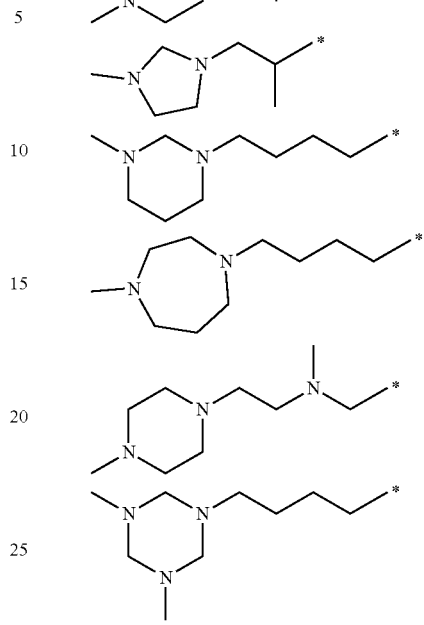

wherein the mark * indicates the position bonding, to —CHR₂.

4. The compound according to claim 1, wherein said $L^{R1}$ is represented by the following formula (1-R1):

$$-(CH_2)_{r1}- \qquad (1\text{-R1})$$

wherein
r1 is an integer of 1 to 10.

5. The compound according to claim 4, wherein said r1 is an integer of 4 to 8.

6. The compound according to claim 1, wherein the longest molecular chain contained in said R consists of 8 or more atoms.

7. The compound according to claim 1, which is represented by any of the following formulas (1-01), (1-02), (1-04) to (1-14), (1-16), and (1-19) to (1-21):

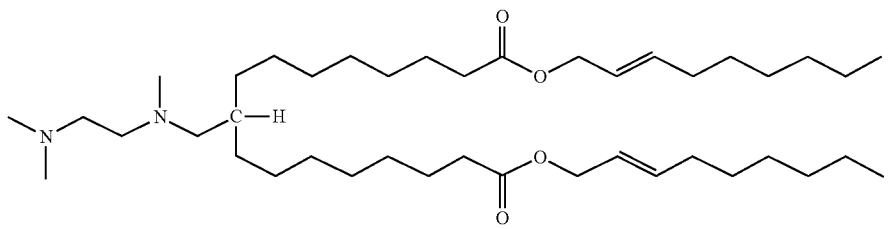

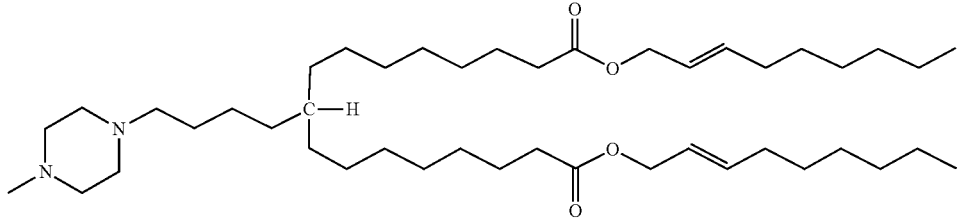

-continued
(1-04)
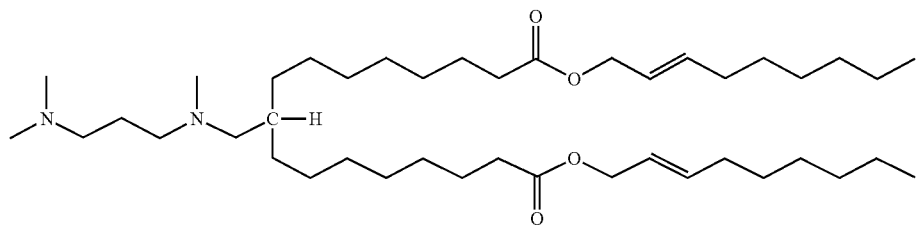
(1-05)
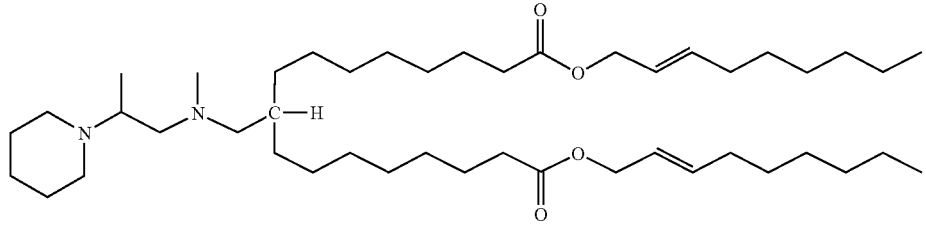
(1-06)
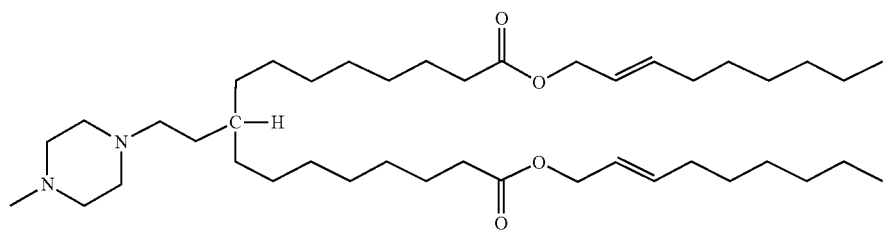
(1-07)
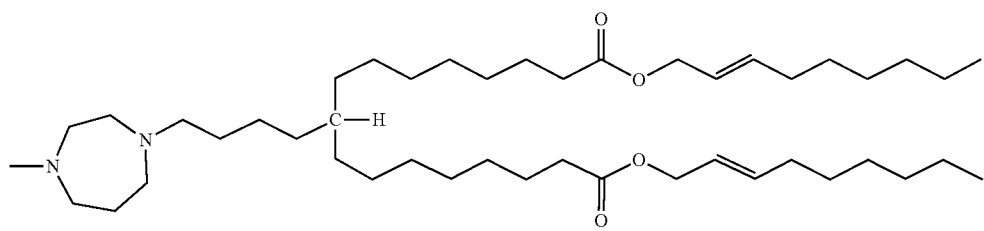
(1-08)
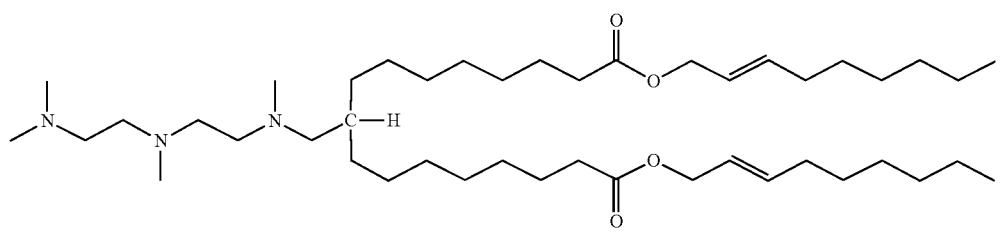
(1-09)
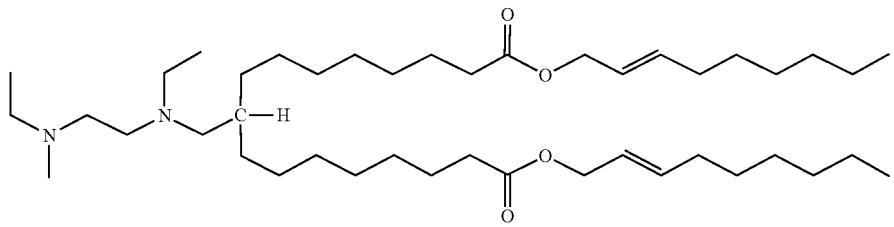
(1-10)
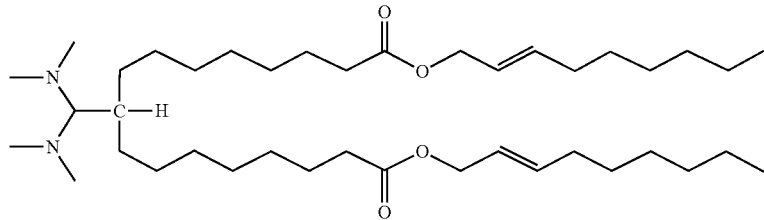

(1-11)
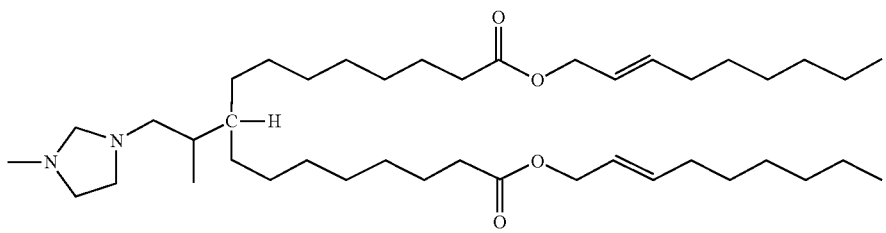
(1-12)
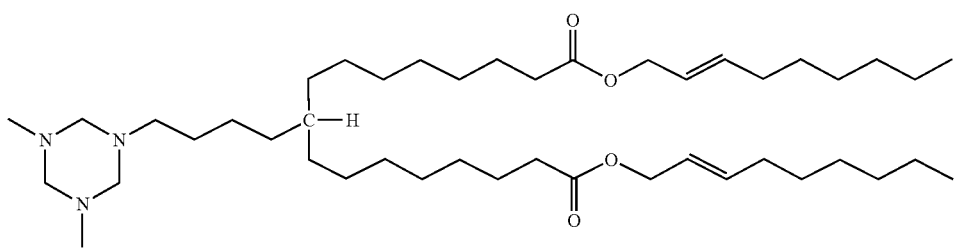
(1-13)
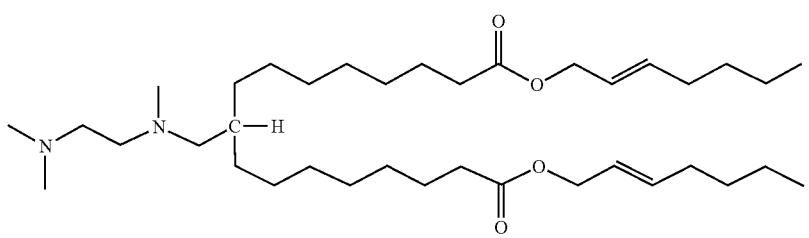
(1-14)
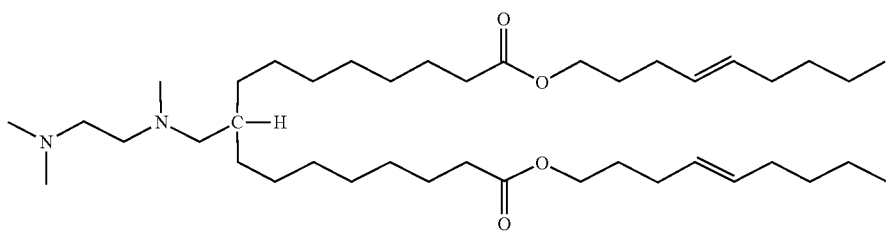
(1-16)
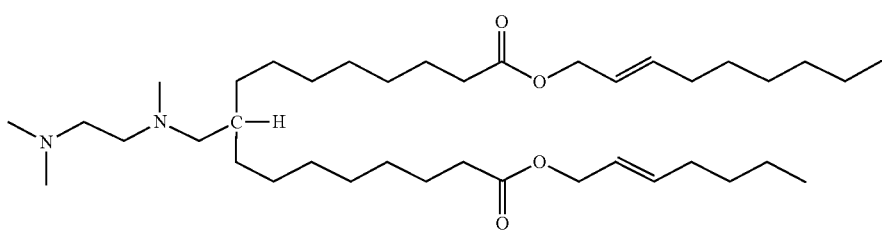
(1-19)
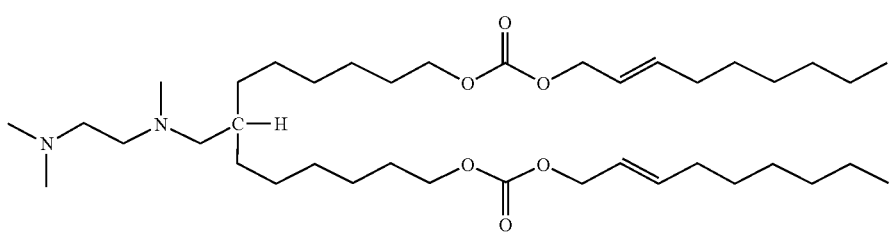

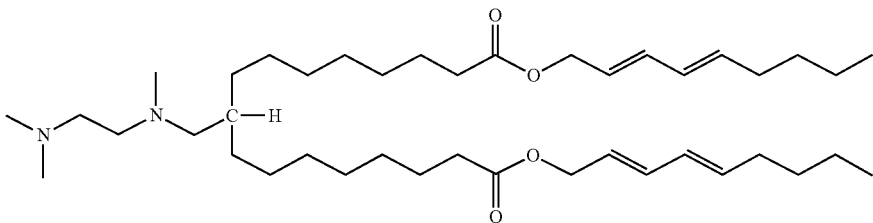

(1-20)

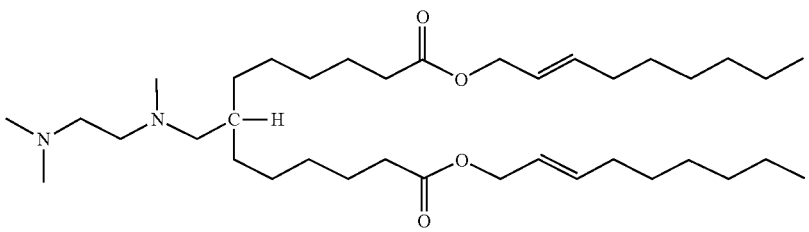

(1-21)

8. Lipid particles containing the compound according to claim 1.

9. The lipid particles according to claim 8, which further contain a compound represented by the following formula (2):

wherein
P is an alkyleneoxy having one or more ether bonds in the main chain,
each X is independently a divalent linking group having a tertiary amine structure,
each W is independently a $C_1$ to $C_6$ alkylene,
each Y is independently a divalent linking group selected from the group consisting of single bond, ether bond, carboxylic ester bond, thiocarboxylic ester bond, thioester bond, amide bond, carbamate bond, and urea bond
each W' is independently a single bond or a $C_1$ to $C_6$ alkylene, and
each Z is independently a liposoluble vitamin residue, a sterol residue, or a $C_{12}$ to $C_{22}$ aliphatic hydrocarbon group;
provided that
the structure further contains at least one biodegradable group selected from the group consisting of carboxylic ester bond, thiocarboxylic ester bond, dithiocarboxylic bond, amide bond, carbamate bond, carboxydioxy bond, and urea bond.

10. The lipid particles according to claim 9, wherein said P contains 3 to 8 carbons and 1 to 2 oxygens.

11. The lipid particles according to claim 9, wherein said each X is independently selected from the group consisting of methylimino, 1,2-pyrrolidinediyl and 1,3-pyrrolidinediyl.

12. The lipid particles according to claim 9, wherein said each Z is a liposoluble vitamin residue or a sterol residue.

13. The lipid particles according to claim 8, which further contain a lipid forming a membrane and a lipid capable of reducing aggregation.

14. The lipid particles according to claim 13, wherein said lipid forming a membrane is selected from the group consisting of:
1,2-dioleoyl-sn-glycero-3-phosphoethanolamine (DOPE),
1,2-stearoyl-sn-glycero-3-phosphoethanolamine (DSPE),
1,2-dipalmitoyl-sn-glycero-3-phosphatidylcholine (DPPC),
1-palmitoyl-2-oleoyl-sn-glycero-3-phosphatidylcholine (POPC),
1,2-di-o-octadecyl-3-trimethylammoniumpropane (DOTMA),
1, 2-dioleoyl-3-dimethylammoniumpropane (DODAP),
1,2-dimyristoyl-3-dimethylammoniumpropane (14:0 DAP),
1,2-dipalmitoyl-3-dimethylammoniumpropane (16:0 DAP),
1,2-distearoyl-3-dimethylammoniumpropane (18:0 DAP),
N-(4-carboxybenzyl)-N,N-dimethyl-2,3-bis(oleoyloxy)-propane (DOBAQ),
1, 2-dioleoyl-3-trimethylammoniumpropane (DOTAP),
1,2-dioleoyl-sn-glycero-3-phosphochlorin (DOPC),
1,2-dilinoleoyl-sn-glycero-3-phosphochlorin (DLPC),
1,2-dioleoyl-sn-glycero-3-phospho-L-serine (DOPS), and cholesterol:
and
said lipid capable of reducing aggregation is a polyethylene glycol (PEG)-modified lipid.

15. The lipid particles according to claim 8, which furthermore contain an activator.

16. The lipid particles according to claim 15, wherein said activator is a nucleic acid selected from the group consisting of plasmid, oligonucleotide, polynucleotide, siRNA, microRNA, DNA, mRNA, aptamer, and ribozyme.

17. The lipid particles according to claim 15, wherein said activator contains a combination of at least one DNA and at least one RNA.

18. The lipid particles according to claim 16, which further contain a compound combinable with the nucleic acid.

19. The lipid particles according to claim 18, wherein said compound combinable with the nucleic acid is a basic protein or a basic peptide.

20. The lipid particles according to claim 18, wherein said compound combinable with the nucleic acid is protamine or histone.

21. The lipid particles according to claim 18, which further contain a compound controlling expression of the nucleic acid in cells.

22. A composition characterized by comprising the lipid particles according to claim 8 and a medium.

23. A composition for delivering, activators to cells, comprising the lipid particles according to claim 8 and a medium.

24. The composition according to claim 23, wherein said lipid particles contain both the compounds of the formulas (1) and (2).

25. The composition according to claim 24, wherein the mole ratio of the content of the compound of the formula (2) to that of the compound of the formula (1) is less than 1.

26. The composition according to claim 23, wherein said cells are tumor cells.

27. The lipid particles according to claim 8, which are used for delivering activators to cells.

28. The lipid particles according to claim 27, which contain both the compounds of the formulas (1) and (2).

29. The lipid particles according to claim 28, wherein the mole ratio of the content of the compound of the formula (2) to that of the compound of the formula (1) is less than 1.

30. The lipid particles according to claim 27, wherein said cells are tumor cells.

31. A method for delivering activators to cells, wherein the activator-containing lipid particles according to claim 8 are brought into contact with the cells.

32. The method according to claim 31, wherein said lipid particles are administered to the subject.

33. The method according to claim 31, wherein said lipid particles contain both the compounds of the formulas (1) and (2).

34. The method according to claim 33, wherein the mole ratio of the content of the compound of the formula (2) to that of the compound of the formula (1) is less than 1.

35. The method according to claim 31, wherein said cells are tumor cells.

\* \* \* \* \*